(12) United States Patent
Gullberg

(10) Patent No.: US 7,485,429 B1
(45) Date of Patent: Feb. 3, 2009

(54) INTEGRIN HETERODIMER AND AN ALPHA SUBUNIT THEREOF

(75) Inventor: Donald Gullberg, Uppsala (SE)

(73) Assignee: Cartela R&D AB, Lund (SE)

( * ) Notice: Subject to any disclaimer, the term of this patent is extended or adjusted under 35 U.S.C. 154(b) by 27 days.

(21) Appl. No.: 09/980,403

(22) PCT Filed: May 31, 2000

(86) PCT No.: PCT/SE00/01135

§ 371 (c)(1),
(2), (4) Date: Apr. 15, 2002

(87) PCT Pub. No.: WO00/75187

PCT Pub. Date: Dec. 14, 2000

(30) Foreign Application Priority Data

Jun. 3, 1999 (SE) .................................... 9902056

(51) Int. Cl.
*G01N 33/53* (2006.01)
*A61K 38/04* (2006.01)
*C07K 14/00* (2006.01)
*C07K 17/00* (2006.01)

(52) U.S. Cl. ...................... 435/7.1; 530/324; 530/350; 530/395

(58) Field of Classification Search .................. 530/350, 530/325; 514/8, 13
See application file for complete search history.

(56) References Cited

U.S. PATENT DOCUMENTS

| 5,304,603 | A | * | 4/1994 | Cheng et al. .................. 514/12 |
| 5,686,059 | A | * | 11/1997 | Goetinck et al. | |
| 5,726,290 | A | * | 3/1998 | Bodary et al. ................ 530/350 |
| 5,968,770 | A | * | 10/1999 | Falb et al. ................... 435/69.1 |
| 6,030,947 | A | * | 2/2000 | Corbi et al. ................... 514/12 |
| 6,046,316 | A | * | 4/2000 | Trikha et al. ................ 536/23.5 |
| 2003/0055231 | A1 | | 3/2003 | Ni et al. | |
| 2003/0129685 | A1 | | 7/2003 | Ni et al. | |
| 2005/0260702 | A1 | | 11/2005 | Pan et al. | |
| 2006/0099622 | A1 | | 5/2006 | Ni et al. | |
| 2006/0122373 | A1 | | 6/2006 | McCarthy et al. | |
| 2006/0275287 | A1 | | 12/2006 | St Croix et al. | |
| 2007/0037206 | A1 | | 2/2007 | Rosen et al. | |

FOREIGN PATENT DOCUMENTS

| WO | 92/19647 A1 | 11/1992 |
| WO | 97/18838 A1 | 5/1997 |
| WO | 98/22500 A2 | 5/1998 |
| WO | WO 0029435 A1 * | 5/2002 |

OTHER PUBLICATIONS

Attwood TK. Genomics. The Babel of bioinformatics. Science. 290(5491):471-473, 2000.*
Kuntz. Structure-based strategies for drug design and discovery. Science. 1992 257(5073):1078-1082.*
Skolnick et al. From genes to protein structure and function: novel applications of computational approaches in the genomic era. Trends Biotechnol. 18(1):34-9, 2000.*
Miller et al., Ligand binding to proteins: the binding landscape model. Protein Sci. Oct. 1997;6(10):2166-79.*
Tiger et al. alpha11beta1 integrin is a receptor for interstitial collagens involved in cell migration and collagen reorganization on mesenchymal nonmuscle cells. Dev. Biol. Sep. 1, 2001;237(1):116-29.*
Alberst et al. Molecular Biolgoy of the cell. $2^{nd}$ ed. pp. 163-196, 258-271 & 821-823, 1989.*
Wier et al. Handbook of Experimental immunology vol. 1: Immunochemistry, 1986, pp. 8.14-8.15.*
Michele Genini et al, "Isolation of genes differentially expressed in human primary myoblasts and embryonal rhabdomyosarcoma," Int. J. Cancer, vol. 66, 1996, pp. 571-577.
Donald Gullberg, et al, "Up-Regulation of a Novel Integrin α-Chain ($α_{mt}$) on Human Fetal Myotubes," Developmental Dynamics, vol. 204, 1995, pp. 57-65.
Lisbet Camper, et al, "Isolation, Cloning, and Sequence Analysis of the Integrin Subunit α 10, a β1-associated Collagen Binding Integrin Expressed on Chondrocytes," The Journal of Biological Chemistry, vol. 273, No. 32, 1998, pp. 20383-20389.
Donald Gullberg et al, "Integrins During Muscle Development and in Muscular Dystrophies," Frontiers in Bioscience, vol. 3, Oct. 1998, pp. 1039-1050.
Teet Velling et al, "cDNA Cloning and Chromosomal Localization of Human $α_{11}$ Integrin," The Journal of Biological Chemistry, vol. 274, No. 36, Sep. 1999, pp. 25735-25742.
K. Lehnert et al, "Cloning, sequence analysis, and chromosoma localization of the novel human integrin alpha subunit (ITGA11)," National Library of Medicine, Sep. 1999.

* cited by examiner

*Primary Examiner*—Maher M Haddad
(74) *Attorney, Agent, or Firm*—Finnegan, Henderson, Farabow, Garrett & Dunner, L.L.P.

(57) ABSTRACT

A recombinant or isolated integrin heterodimer comprising a novel subunit α11 in association with a subunit β is described. The integrin or the subunit α11 can be used as marker or target of all types of cells. The integrin or subunit α11 thereof can be used as marker or target in different physiological or therapeutic methods. They can also be used as active ingredients in pharmaceutical compositions and vaccines.

7 Claims, 13 Drawing Sheets

Figures 1A, 1B:
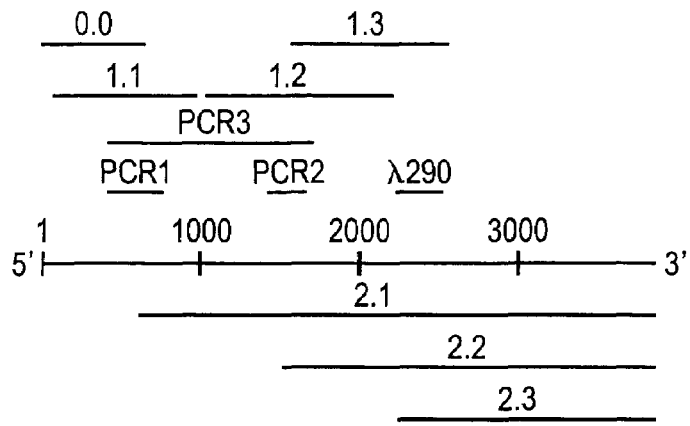

| PCR Fragm./<br>CDNA clones | nt. positions |
|---|---|
| PCR1 | 388-731 |
| PCR2 | 1575-1774 |
| PCR3 | 388-1774 |
| 5'RACE | 1-540 |
| G6 library | 1-641 |
| 1.1 | 53-1007 |
| 1.2 | 1018-2188 |
| 1.3 | 1553-2563 |
| 2.1 | 451-3837 |
| 2.2 | 1590-3983 |
| 2.3 | 2315-3983 |

GGCACGAGGCGCGCGAGGAGGCTGCGCTCGGCTTGCCAGTCCCCGCTGCACACCGGACCCGCCCGCCCCCAGGGGCCATGGACCTGCCCAGGGGCCTGGTGGTGGCC 120
                                                                              M  D  L  P  R  G  L  V  V  A   10

TGGGCGCTCAGCTGTGGCCAGGGTTCACGGACACCTTCAACATGGACACCAGGAAGCCCCGGGTCATCCCTGGCTACACAGTGCAGCAGCACGACATC 240
 W  A  L  S  L  W  P  G  F  T  D  T  F  N  M  D  T  R  K  P  R  V  I  P  G  S  R  T  A  F  F  G  Y  T  V  Q  Q  H  D  I   50

AGTGGCAATAAGTGGCTGGTCGTGGGCGGCCCCACTGGAAACCAATGGCTACCAGAAGACGGGAGACGTGTACAAGTGTCCAGTGATCCACGGGAACTGCACCAAACTCAACCTGGGAAGG 360
 S  G  N  K  W  L  V  V  G  A  P  L  E  T  N  G  Y  Q  K  T  G  D  V  Y  K  C  P  V  I  H  G  N* C  T  K  L  N  L  G  R   90

GTCACCCTGTCCAAGTGTCCAGCGGAAAGAGACAACATGCGCCTCGGCCTTAGTCTGGCCACCAACCCCAAGGACAACAGCTTCCTGGCTTGCAGCCCCCTCTGGTCTCATGAGTGTGGG 480
 V  T  L  S  N* V  S  E  R  K  D  N  M  R  L  G  L  S  L  A  T  N  P  K  D  N  S  F  L  A  C  S  P  L  W  S  H  E  C  G   130

AGCTCCTACTACACAGGGATGTGTTCAAGAGTCAACTCCAACTTCAGGTTCTCCAAGACCGTGGCCCCAGCTGCCTTGCAGAGACTGTCATTGTCCTGGAT 600
 S  S  Y  Y  T  G  M  C  S  R  V  N  S  N  F  R  F  S  K  T  V  A  P  A  L  Q  R  C  Q  T  Y  M  D  I  V  I  V  L  D   170

GGCTCCAACAGCATCTACCCCTGGGTGGAGGTTCAGCACTTCCTCATCAACATCCTGAAAAAGTTTTACATTGGCCCAGGGCAGATCCAGGTTGTGCAGTTTGTGCAGTATGGGGAAGATGTG 720
 G  S  N  S  I  Y  P  W  V  E  V  Q  H  F  L  I  N  I  L  K  K  F  Y  I  G  P  G  Q  I  Q  V  V  Q  Y  G  E  D  V   210

GTGCATGAGTTTCACCTCAACGACTACAGGTCTGTAAAAGATGTGGTGGAAGCTGCCAGCCACATTGAGCAGAGAGGAGGAACAGAGACCCGGACGGCCATTGGCATTGAATTTGCACGC 840
 V  H  E  F  H  L  N  D  Y  R  S  V  K  D  V  V  E  A  A  S  H  I  E  Q  R  G  G  T  E  T  R  T  A  F  G  I  E  F  A  R   250

SEQ ID No. 1
FIG. 2A

```
TCAGAGGCTTTCCAGAAGGGTGGAAGGAGGAGCCAAGAAGAAAGGTGATGATTGTCATCACAGATGGGGAGTCCCACGACAGCCCAGACCTGGAGAAGGTGATCCAGAGCGAAAGCGAAAGAGAC  960
 S  E  A  F  Q  K  G  G  R  K  G  A  K  K  V  M  I  V  I  T  D  G  E  S  H  D  S  P  D  L  E  K  V  I  Q  Q  S  E  R  D        290

AACGTAACAAGATATGCGGTGGCCGTCCTGGGCTACTACAACCCCAGGGGGATCAATCCAGAAACTTTTCTAAATGAAATCAAATACATCGCCAGTGACCCTGATGACAAGCACTTCTTC  1080
N* V  T  R  Y  A  V  A  V  L  G  Y  Y  N  R  R  G  I  N  P  E  T  F  L  N  E  I  K  Y  I  A  S  D  P  D  D  K  H  F  F        330

AATGTCACTGATGAGGCTGCCTTGAAGGACATTGTCGATGCCCTGGGGGACAGAATCTTCAGCCTGGAAGGCACCAACAAGAACGAGACCTCCTTTGGGCTGGAGATGTCACAGACGGGC  1200
N* V  T  D  E  A  A  L  K  D  I  V  D  A  L  G  D  R  I  F  S  L  E  G  T  N  K* E  T  S  F  G  L  E  M  S  Q  T  G         370

TTTTCCTCGCACGTGGTGGAGGATGGGGTTCTGCTGGGAGCCGTCGGTGCCTATGACTGGAATGGAGCAGTGCTCAAAGGAGACGAGTCTGCCGGGAAGGTCATTCCTCTCCGGGAGTCCTAC  1320
 F  S  S  H  V  V  E  D  G  V  L  L  G  A  V  G  A  Y  D  W  N  G  A  V  L  K  E  T  S  A  G  K  V  I  P  L  R  E  S  Y     410

CTGAAAGAGTTCCCCGAGGAGCTCAAGAACCATGGTGCATACCTGGGGTACACAGTCACATCGGTCCTCCAGGCAGGGCGAGTGTACGTGGCCGGAGCCCCCGTTCAACCAC  1440
 L  K  E  F  P  E  E  L  K  N  H  G  A  Y  L  G  Y  T  V  T  S  V  V  S  S  R  Q  G  R  V  Y  Y  V  A  G  A  P  R  F  N* H   450

ACGGGCAAGGTCATCCTGTTCACCATGCACAACAACCGAGAGCCTCACCATCCACCAGGCCTATGGGGGCTATGCCCAGAGATAGGCTCTACTTTGGGAGTGAAATCACCTCGGTGGACATCGAC  1560
 T  G  K  V  I  L  F  T  M  H  N  N* R  S  L  T  I  H  Q  A  M  R  G  Q  Q  I  G  S  Y  F  G  S  E  I  T  S  V  D  I  D     490

GGCGACGGCGTGATGTCCTGCTGGTGGGCGCACCCATGTACTTCAACGAGGGCCGTGAGCGAGGAAGGCAAGGTGTACGTCTATGAGCTGAGACAGAACCGGTTTGTTTATAACGGAACG  1680
 G  D  G  V  I  D  V  L  L  V  G  A  P  M  Y  F  N  E  G  R  E  R  G  K  V  Y  V  Y  E  L  R  Q  N  R  F  V  Y  N* G  T     530
```

SEQ ID No. 1

FIG. 2B

```
CTAAAGGATTCACACAGTTACCAGAATGCCCGATTTGGGTCCTCCATTGCCTCAGTTCGAGACCTCAACCAGGATTCCTACAATGACGTGGTGGTGGGAGCCCCTCTGGAGGACAACCAC 1800
 L  K  D  S  H  S  Y  Q  N  A  R  F  G  S  S  I  A  S  V  R  D  L  N  Q  D  S  Y  N  D  V  V  V  G  A  P  L  E  D  N  H   570

GCAGGAGGCCATCTACATCTTCCACGGGCTTCCGAGGCAGCAGCATCCTGAAGACCTAAGCAGAGAATCACAGCACTTAAGCAGAGCTGGCTACCGGGCTCCAGTATTTTGGCTGCAGCATCCACGGG 1920
 A  G  A  I  Y  I  F  H  G  F  R  G  S  I  L  K  T  P  K  Q  R  I  T  A  S  E  L  A  T  G  L  Q  Y  F  G  C  S  I  H  G   610

CAATTGGACCTCAATGAGGATGGGCTCATCGACCTGGCAGTGGGAGCCCTTGGCAACGTGTGATTCTGTGGTCCCGCCAGTGGTTCAGATCAATGCCAGCCTCCACTTTGAGCCATCC 2040
 Q  L  D  L  N  E  D  G  L  I  D  L  A  V  G  A  L  G  N  A  V  I  L  W  S  R  P  V  V  Q  I  N* A  S  L  H  F  E  P  S   650

AAGATCAACATCTTCCACAGAGACTGCAAGCGCAGTGGCAGGGATGCCACCTGCCTGGCCGCCTTCCTGCTCTTCACGCCCATCTTCCAAACAACAACTGTTGGC 2160
 K  I  N  I  F  H  R  D  C  K  R  S  G  R  D  A  T  C  L  A  A  F  L  C  F  T  P  I  F  L  A  P  H  F  Q  T  T  T  V  G   690

ATCAGATACAACGCCACCATGGATGAGAGGCGGTATACACCGAGGCCCACCTGGACGAGAGGGCGGGACCGATTCACCAACAGAGCTGCTCTCCGGCAGGAGCTCTGTGAG 2280
 I  R  Y  N* A  T  M  D  E  R  R  Y  T  P  R  A  H  L  D  E  G  G  D  R  F  T  N  R  A  V  L  L  S  S  G  Q  E  L  C  E   730

CGGGATCAACTTCCATGTCCTGGACACTGCTGACTACGTCAAGCCAGTGACCTTCTCAGTGAGTATTCCCTGGAGGACCCTGACTATGGCCCCATGCTGGACGACGGGCTGGCCCACACT 2400
 R  I  N  F  H  V  L  D  T  A  D  Y  V  K  P  V  T  F  S  V  E  Y  S  L  E  D  P  D  H  G  P  M  L  D  D  G  W  P  T  T   770

CTCAGAGTCTCGGTGCCCTTCTGGAACGGCTGCAATGAGGATGAGCACTGTGTCCTGACCTGTGTTGATGCCCGAGTGACCTGCCACGGCCATGGAGTACTGCCAGAGGGTGCTG 2520
 L  R  V  S  V  P  F  W  N  G  C  N  E  D  E  H  C  V  P  D  L  V  L  D  A  R  S  D  L  P  T  A  M  E  Y  C  Q  R  V  L   810
```

SEQ ID No. 1

FIG. 2C

```
AGGAAGCTGCCGCAGGACTGCTCCGCATACACGCTGTCCTTCGACACCACAGTCTTCATCATAGAGAGCACACGCCAGTGGCGGTGAGGCCACACTGGAGAACAGGGGCGAGAAC  2640
 R  K  P  A  Q  D  C  S  A  Y  T  L  S  F  D  T   T  V  F  I  I  E  S  T  R  Q  R  V  A  V  E  A  T  L  E  N  R  G  E  N    850

GCCTACAGTACGGTCCTAAATATCCGCAGTCAGCAAACCTGCAGTTTGCCAGCCTGATCCAGAAGGAGGACTCAGACGGTAGCATTGAGTGTGTGAACGAGGAGGAGGCTCCAGAAG  2760
 A  Y  S  T  V  L  N* I  S  Q  S  A  N  L  Q  F  A  S  L  I  Q  K  E  D  S  D  G  S  I  E  C  V  N  E  E  R  R  L  Q  K    890

CAAGTCTGCAACGTCAGCTATCCCTTCTTCCGGGCCAAGGCCAAGGTGGCTTTCCGTCTTGATTCCGAGTTCAGCAAATCCATCTTCCTACACCACCTGGAGATCGAGCTGCTGCAGGC  2880
 Q  V  C  N* V  S  Y  P  F  F  R  A  K  A  K  V  A  F  R  L  D  S  E  F  S  K  S  I  F  L  H  H  L  E  I  E  L  A  A  G    930

AGTGACAGTAATGAGCGGGACAGCAGCAAGGAAGACAACGTGGCCCCCCTTACGCTTCCACCTCAAATACGAGGCTGACGTCCTCTTCACCAGGAGCAGCAGCCTGAGCCACTACGAGGTC  3000
 S  D  S  N  E  R  D  S  T  K  E  D  N  V  A  P  L  R  F  H  L  K  Y  E  A  D  V  L  F  T  R  S  S  S  L  S  H  Y  E  V    970

AAGCTCAACAGTCTGGAGAGATACGATGGTATCGGGCCTCCCTTCAGCATCTTCAGGATCCAGAACTGGGCTTGTTCCCCATCCAGCGATGATGAAGATCACCATTCCC  3120
 K  L  N* S  S  L  E  R  Y  D  G  I  G  P  P  F  S  C  I  F  R  I  Q  N  L  G  L  F  P  I  H  G  M  M  M  K  I  T  I  P    1010

ATCGCCACCAGGAGCGGCAACCGCCTACTGAAGCTGAGGGACTTCCTCACGGACGAGGCGAACACGTCCTGTAACATCTGGGGCAATAGCACTGAGTACCGGCCACCCCAGTGGAGGAA  3240
 I  A  T  R  S  G  N  R  L  L  K  L  R  D  F  L  T  D  E  A  N* T  S  C  N  I  W  G  N* S  T  E  Y  R  P  T  P  V  E  E    1050

GACTTGCGTCGTCCACAGCTGAATCACAGCAACTCTGATGTCGTCTCATCAACTGCAATATACGGCTGGTCCCCAACCAGGAAATCAATTTCCATCTACTGGGAACCTGTGGTTG  3360
 D  L  R  R  A  P  Q  L  N* H  S  N  S  D  V  V  S  I  N  C  N  I  R  L  V  P  N  Q  E  I  N  F  H  L  G  N  L  W  L    1090
```

SEQ ID No. 1

FIG. 2D

```
AGGTCCCTAAAAGCACTCAAGTACAAATCATGAAAATCATGGTCAACGCAGCCTTGCAGAGGCAGTTCCACAGCCCCTTCATCTTCCGTGAGGAGGATCCAGCGCCACAGATCGAGTTT  3480
 R  S  L  K  A  L  K  Y  K  S  M  K  I  M  V  N  A  A  L  Q  R  Q  F  H  S  P  F  I  F  R  E  E  D  P  S  R  Q  I  E  F   1130

GAGATCTCCAAGCAAGAGGACTGGCAGGTCCCCATCTGGATCATTGTAGGCAGCACCCTGGGGGGCCTCCTACTGCTGGCCCTGCTGGTCCTGGCACTGCGGAAGCTCGGCTTCTTTAGA  3600
 E  I  S  K  Q  E  D  W  Q  V  P  I  W  I  I  V  G  S  T  L  G  G  L  L  L  L  A  L  L  V  L  A  L  R  K  L  G  F  F  R   1170

AGTGCCAGGCGCAGGAGGCGAGCCTGGTCTGGACCCCACCCCAAAGTCTGGAGTGAGGCTCCAGAGGAGACTTTGAGTTGATGGGGGCCAGGACACCAGTCCAGGTAGTGTTGAGACCC  3720
 S  A  R  R  R  R  E  P  G  L  D  P  T  P  K  V  L  E   1188

AGGCCTGTGGGCCCCACCGAGCTGGAGCGGGAGAGAGGAAGCCAGGTGGCTTTGCACTTGACCTCATCTCCGAGCAATGGCGCCTGCTCCTCCCTCCAGAATGGAACTCAAGCTGGTTTTAAGTGG  3840

AACTGCCTACTGGGAGACTGGGACACCTTTACACAGACCCCTAGGGATTTAAAGGGACACCCCTACACACACCCCAAGGCCTCCCTCAGGCTCTGTGGAGGGCATTTGCT  3960

GCCCCAGCTACTAAGGTGCTAGG  3983
```

SEQ ID No. 1

FIG. 2E

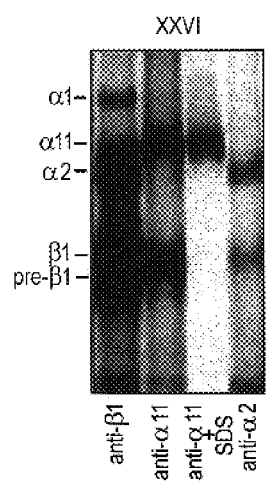
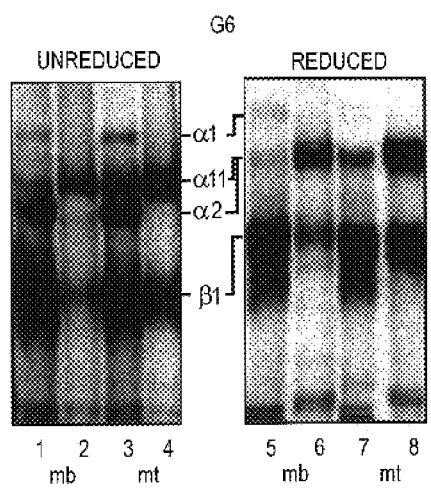
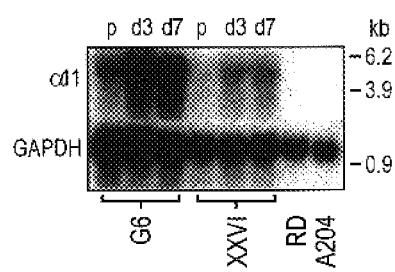
FIG. 6A
FIG. 6B
FIG. 6C

INTEGRIN HETERODIMER AND AN ALPHA SUBUNIT THEREOF

FIELD OF THE INVENTION

The present invention relates to a recombinant or isolated integrin heterodimer comprising a subunit α11 and a subunit β, the subunit α11 thereof, homologues and fragments of said integrin and of said subunit α11, processes of producing the same, polynucleotides and oligonucleotides encoding the same, vectors and cells comprising the same, binding entities binding specifically to binding sites of the same, and the use of the same.

BACKGROUND OF THE INVENTION

Integrins are heterodimers composed of non-covalently associated α- and β-chains which connect cells to the extracellular matrix or to other cells (1). In addition to acting as mechanical links between the cytoskeleton and extracellular ligands, integrins are signal transducing receptors which influence processes such as cell proliferation, cell migration and cell differentiation (2-4). Integrins can be grouped into subfamilies based on shared β-chains, shared ligand binding properties, or shared structural features of the α-chains. Currently 17 α-chains and 8 β-chains have been identified (5). Of the subfamilies with shared β-chains, the Pβ1 subfamily has the most members. To date, 11 integrin α-chains associated with the β1-chain have been identified and characterized, α1-α10 and αv (5).

Several integrins bind the sequence RGD in their respective ligands (1). Of those integrins identified so far, α4-, α5-, α8-, αIIb- and αv-chains form heterodimers that mediate RGD-dependent interactions. The ligands containing RGD are generally found in the interstitial type of extracellular matrix. Major non-RGD dependent ligands include various collagen and laminin isoforms. Although both collagens and laminins contain the RGD sequence in their primary sequences, these RGD sequences are cryptic (6-9) and normally not accessible to cells in the native proteins, but they may be exposed during growth and reorganization events of the extracellular matrix.

Another subdivision of integrins can be made based on structural similarities of the α-chains. A number of integrins contain an extracellular I-domain (10, 11) which is homologous to collagen binding A-domains present in von Willebrand factor (12). The I-domain constitutes an inserted domain of approximately 200 amino acids which is present in 8 known integrins (α1, α2, α10, αL, αM, αX, αD and αE) (5, 10). Structural analysis of integrin I-domains crystallized in the presence of $Mg^{2+}$ have revealed the presence of a characteristic "MIDAS" (metal ion dependent adhesion site) motif, shown to be critical for ligand binding (13). Integrin α-chains containing the I-domain are not cleaved into heavy and light chains, although the rat α1 chain possesses a proteolytic cleavage site near the membrane spanning region (14, 15). For I-domain integrins the principal ligand binding sites are found within the I-domain (10). Known ligands for I-domains found within the β1 integrin subfamily include laminins and collagens (α1β1 and α2β1 integrins) (16-19), and Echovirus (α2β1 integrin) (20).

Structure comparisons have suggested that integrins fold into a so-called 7-bladed β-propeller structure which forms one globular domain with the ligand binding region on the upper surface (21). The I-domain is inserted between blade 2 and 3 in this propeller and divalent cation binding sites are located on the lower surface in blades 4-7 (22, 23). Studies of β2 integrins have revealed that proper folding of the β2-chain is dependent on the presence of the αL-chain but that the I-domain folds independently of other structural elements in the α- and β-chains (24). In integrin α-chains, a less conserved stalk region separates the predicted β-propeller from the short transmembrane region. This stalk region is possibly involved in transducing conformational changes between the extracellular and intracellular regions, as well as mediating protein-protein interactions. Although integrins take part in cell signalling events, the cytoplasmic tail is short and lacks enzymatic activity. The sequence GFFKR is conserved in a majority of integrin α-subunits cytoplasmic tails and has been shown to be important for calreticulin binding (25).

Cellular interactions with the extracellular matrix during muscle formation and in muscular dystrophy have received increased interest during the past years. In the early 1960's a mutant was described in *Drosophila* which was characterized by the detachment of muscles from their attachment points at the time of the first embryonic muscle contraction, causing the embryos to assume a spheroid shape (26). The mapping of the molecular defect in the lethal myospheroid mutant in 1988 to an integrin β-chain (27), was the first evidence for a role of integrins in maintaining muscle integrity. More recently, refined analysis of Drosophila mutants have indicated distinct roles for integrins in muscle endpoint attachments and sarcomere structure (28). The Drosophila integrins are all cleaved α-chains and share many features with vertebrate integrins such as the ability to cluster into focal contacts (29).

The finding that inactivation of the α7 integrin gene in mouse (30), as well as mutations in the human ITGA7 gene (31), both cause muscular dystrophy affecting mainly muscle attachment points, indicates a striking conservation of integrin function during evolution. Of the 11 members of the β1 subfamily, α7 exists as a major integrin α-chain (32, 33) associated with the β1D integrin chain in the adult skeletal muscle sarcolemma (34). Intriguingly, mutations in the basement membrane protein laminin α2-chain (35-37) cause a more severe disease than that observed for the laminin receptor integrin α7β1 (30). This indicates that other receptors for laminins exist in muscle.

A novel integrin has recently been identified on cultured human fetal muscle cells (38). The present invention is related to, inter alia, the cloning and characterization of this novel I-domain containing, β1-associated integrin chain, which is expressed in muscle tissues.

SUMMARY OF THE INVENTION

The full-length cDNA for this integrin subunit, α11, has now been isolated. The open reading frame of the cDNA encodes a precursor of 1188 amino acids. The predicted mature protein of 1166 amino acids contains 7 conserved FG-GAP repeats, an I-domain with a MIDAS motif, a short transmembrane region and a unique cytoplasmic domain of 24 amino acids containing the sequence GFFRS. α11, like other I-domain integrins, lacks a dibasic cleavage site for generation of a heavy and a light chain, and contains three potentional divalent cation binding sites in repeats 5-7. The presence of 22 inserted amino acids in the extracellular stalk portion (amino acids 804-826) distinguishes the α11 integrin sequence from other integrin α-chains. Amino acid sequence comparisons reveal the highest identity of 42% with α10 integrin chain. Immunoprecipitation with antibodies to α11 integrin captures a 145 kD protein, distinctly larger than the 140 kD α2 integrin chain when analyzed by SDS-PAGE under non-reducing conditions. Fluorescense in situ hybridization maps the integrin α11 gene to chromosome 15q23, in the vicinity of an identified locus for Bardet-Biedl syndrome. Based on Northern blotting integrin α11 mRNA levels are high in adult human uterus and in heart, and intermediate in skeletal muscle and some other tissues tested. During in vitro myogenic differentiation, α11 mRNA and protein are up-regulated. Studies of ligand binding properties show that α11β1 binds collagen type I Sepharose and cultured muscle cells localize α11β1 into focal contacts on collagen type I.

DETAILED DESCRIPTION OF THE INVENTION

The present invention relates in its different aspects to the following:

A recombinant or isolated integrin subunit α11 comprising essentially the amino acid sequence shown in SEQ ID No. 1, or homologues or fragments thereof.

The invention also encompasses integrin homologues of said integrin, isolated from other species, such as bovine integrin heterodimer comprising a subunit α11 in association with a subunit β, preferably β1, as well as homologues isolated from other types of human cells or from cells originating from other species.

The term "homologues" in the context of the present invention is meant to imply proteins of a common evolutionary origin, having identical or similar functions, specifically requiring evidence based on gene structure and not merely a similarity of protein structure.

The invention also encompasses a process of producing a recombinant integrin subunit α11 comprising essentially the amino acid sequence shown in SEQ ID No. 1, or homologues or fragments thereof, which process comprises the steps of a) isolating a polynucleotide comprising a nucleotide sequence coding for an integrin subunit α11, or homologues or fragments thereof, b) constructing an expression vector comprising the isolated polynucleotide, c) transforming a host cell with said expression vector, d) culturing said transformed host cell in a culture medium under conditions suitable for expression of integrin subunit α11, or homologues or fragments thereof, in said transformed host cell, and, optionally, e) isolating the integrin subunit α11, or homologues or fragments thereof, from said transformed host cell or said culture medium. The transformation can be performed in vitro, in situ or in vivo.

In further aspects, the invention encomppases:

A process of providing an integrin subunit α11, or homologues or fragments thereof, whereby said subunit is isolated from a cell in which it is naturally present.

An isolated polynucleotide comprising a nucleotide coding for said integrin subunit α11, or for homologues or fragments thereof, which polynucleotide comprises essentially the nucleotide sequence shown in SEQ ID No. 1 or suitable parts thereof.

An isolated polynucleotide or oligonucleotide which hybridises to a polynucleotide or oligonucleotide encoding said integrin subunit α11 or homologues or fragments thereof, wherein said isolated polynucleotide or oligonucleotide fails to hybridise to a DNA or RNA encoding an integrin subunit α10.

A vector comprising a polynucleotide or oligonucleotide coding for said integrin subunit α11, or homologues or fragments thereof, which polynucleotide or oligonucleotide comprises the nucleotide sequence shown in SEQ ID No. 1 or parts thereof.

A vector comprising a polynucleotide or oligonucleotide which hybridises to a DNA or RNA encoding an integrin subunit α11 or homologues or fragments thereof, wherein said polynucleotide or oligonucleotide fails to hybridise to a DNA or RNA encoding an integrin subunit α10.

A cell containing the vector as defined above.

A cell generated during the process as defined above, in which a polynucleotide or oligonucleotide coding for said integrin subunit α11, or homologues or fragments thereof, which polynucleotide or oligonucleotide comprises essentially the nucleotide sequence shown in SEQ ID No. 1 or parts thereof, has been stably integrated in the cell genome.

Binding sites of the amino acid sequence of the integrin subunit α11, or of homologues or fragments thereof, said binding sites having the capability of binding specifically to entities chosen from the group comprising proteins, peptides, carbohydrates, lipids, natural integrin binding ligands, polyclonal and monoclonal antibodies, and fragments thereof.

Binding entities having the capability of binding specifically to integrin subunit α11 comprising the amino acid sequence of SEQ ID No. 1 or to homologues or fragments thereof, preferably chosen from the group comprising proteins, peptides, carbohydrates, lipids, natural integrin binding ligands, polyclonal and monoclonal antibodies, and fragments thereof.

A recombinant or isolated integrin heterodimer comprising a subunit α11 and a subunit β, in which the subunit α11 comprises essentially the amino acid sequence shown in SEQ ID No. 1, or homologues and fragments thereof. Said subunit β is preferably β1.

A process of producing a recombinant integrin heterodimer comprising a subunit α11 and a subunit β, in which the subunit α11 comprises essentially the amino acid sequence shown in SEQ ID No. 1, or homologues or fragments thereof, which process comprises the steps of a) isolating one polynucleotide comprising a nucleotide sequence coding for a subunit α11 of an integrin heterodimer and, optionally, another polynucleotide comprising a nucleotide sequence coding for a subunit β of an integrin heterodimer, or polynucleotides or oligonucleotides coding for homologues or fragments thereof having similar biological activity, b) constructing an expression vector comprising said isolated polynucleotide coding for said subunit α11 optionally in combination with an expression vector comprising said isolated nucleotide coding for said subunit β, c) transforming a host cell with said expression vector or vectors, which transformation may be performed in vitro, in situ or in vivo, d) culturing said transformed host cell in a culture medium under conditions suitable for expression of an integrin heterodimer comprising a subunit α11 and a sub-unit β, or homologues or fragments thereof, in said transformed host cell, and, optionally, e) isolating the integrin heterodimer comprising a subunit α11 and a subunit β, or homologues or fragments thereof, or the α11 subunit thereof from said transformed host cell or said culture medium.

A process of providing an integrin heterodimer comprising a subunit α11 and a subunit β, or homologues or fragments thereof having similar biological activity, whereby said integrin heterodimer is isolated from a cell in which it is naturally present.

A cell containing i) a first vector, said first vector comprising a polynucleotide or oligonucleotide coding for a subunit α11 of an integrin heterodimer, or for homologues or parts thereof, which polynucleotide or oligonucleotide comprises essentially the nucleotide sequence shown in SEQ ID No. 1 or parts thereof, and ii) a second vector, said second vector comprising a polynucleotide or oligonucleotide coding for a subunit β of an integrin heterodimer, or for homologues or fragments thereof.

Binding sites of an integrin heterodimer as defined above, or of homologues or fragments thereof, said binding sites having the capability of binding specifically to entities chosen among the group comprising proteins, peptides, carbohydrates, lipids, natural integrin binding ligands, polyclonal and monoclonal antibodies, and fragments thereof.

Binding entities having the capability of binding specifically to said integrin heterodimer, or to homologues or fragments thereof, or a subunit α11 thereof. Said subunit β is preferably β1. The binding entities are preferably chosen among the group comprising proteins, peptides, carbohydrates, lipids, natural integrin binding ligands, and fragments thereof.

A fragment of the integrin subunit α11, which fragment is a peptide chosen from the group comprising peptides of the cytoplasmic domain, especially a peptide comprising essentially the amino acid sequence (SEQ ID No. 3) KLGFFRSARRRREPGLDPTPKVLE, of the I-domain, especially a peptide comprising essentially the amino acid sequence from about amino acid No. 159 to about amino acid No. 355 of SEQ ID No. 1, and the extracellular extension region, especially a peptide comprising essentially the amino acid sequence from about amino acid No. 804 to about amino acid No. 826 of SEQ ID No. 1.

A method of producing a fragment of the integrin subunit α11 as defined above, which method comprises a sequential addition of amino acids. This method comprises adding and removing protective groups in a manner known by the man skilled in the art.

A polynucleotide or oligonucleotide coding for a fragment of the integrin subunit α11 as defined above.

Binding sites of a fragment as defined above, said binding sites having the capability of binding specifically to entities chosen from the group comprising proteins, peptides, carbohydrates, lipids, natural integrin binding ligands, and fragments thereof.

Binding entities having the capability of binding specifically to a fragment as defined of the human integrin subunit α11 as defined above. Preferably, said binding entities are chosen from the group comprising proteins, peptides, carbohydrates, lipids, natural integrin binding ligands, and fragments thereof.

A process of using an integrin subunit α11 comprising essentially the amino acid sequence shown in SEQ ID No. 1 or an integrin heterodimer comprising said subunit α11 and a subunit β, or a homologue or fragment of said integrin or subunit, as a marker or target molecule of cells or tissues expressing said integrin subunit α11, which cells or tissues are of animal including human origin. Especially, said subunit β is β1.

In embodiments of this process, said fragment is a peptide chosen from the above defined group.

In one embodiment of said process, the cells are chosen from the group comprising fibroblasts, muscle cells, chondrocytes, osteoblasts, mesenchymally derived cells and stem cells.

Especially, said process is used during pathological conditions involving said subunit α11. Said pathological conditions comprise in one embodiment damage of muscles, muscle dystrophy, fibrosis or wound healing. In another embodiment, said pathological conditions comprise damage of cartilage and/or bone, or cartilage and/or bone diseases. In a still further embodiment, said pathological conditions comprise trauma, rheumatoid arthritis, osteoarthritis or osteoporosis.

In a further embodiment, said process is a process for detecting the formation of cartilage during embryonic development, or for detecting physiological or therapeutic reparation of cartilage and/or muscle, or for selection and analysis, or for sorting, isolating or purification of chondrocytes and/or muscle cells, or for detecting regeneration of cartilage or chondrocytes during transplantation of cartilage or chondrocytes, respectively, or of muscle or muscle cells during transplantation of muscle or muscle cells, respectively, or for studies of differentiation of condrocytes or muscle cells.

Said process may be and in vitro, an in situ or an in vivo process.

A process of using binding entities having the capability of binding specifically to binding sites of an integrin subunit α11 as defined above, or of an integrin heterodimer comprising said subunit α11 and a subunit β, or to homologues or fragments thereof, as markers or target molecules of cells or tissues expressing said integrin subunit α11, which cells or tissues are of animal including human origin. Especially, said subunit β is β1.

In embodiments of this process, said fragment is as defined above.

In one embodiment, said process is a process for detecting the presence of an integrin subunit α11 comprising the amino acid sequence shown in SEQ ID No. 1, or of an integrin heterodimer comprising said subunit α11 and a subunit β, or of homologues or fragments thereof.

Furthermore, embodiments of this process encompass similar embodiments as defined above in connection with the process of using the integrin subunit α11 as a marker or target molecule.

A process for detecting the presence of an integrin subunit α11, or of a homologue or fragment of said integrin subunit, as defined above, on cells, whereby a polynucleotide or oligonucleotide chosen from the group comprising essentially a polynucleotide or oligonucleotide as shown in SEQ ID No. 1 is used as a marker under hybridisation conditions, wherein said polynucleotide or oligonucleotide fails to hybridise to a DNA or RNA encoding an integrin subunit α10. Said cells may be chosen from the group comprising muscle cells.

In embodiments of this process, said fragment is as defined above.

Furthermore, embodiments of this process encompass similar embodiments as defined above in connection with the process of using the integrin subunit α11 as a marker or target molecule.

A pharmaceutical composition comprising as an active ingredient a pharmaceutical agent or an antibody which is capable of using an integrin heterodimer comprising a subunit α11 and a subunit β, or the subunit α11 thereof, or a homologue or fragment of said integrin or subunit α11, as a target molecule.

A pharmaceutical composition comprising as an active ingredient a pharmaceutical agent or an antibody which is capable of stimulating cell surface expression or activation of an integrin heterodimer comprising a subunit α11 and a subunit β, or the subunit α11 thereof, or homologues or fragments of said integrin or subunit α11. In one embodiment, said composition is for use in stimulating, inhibiting or blocking the formation of muscles, cartilage, bone or blood vessels.

A vaccine comprising as an active ingredient at least one member of the group comprising an integrin heterodimer, which heterodimer comprises a subunit α11 and a subunit β, or the subunit α11 thereof, and mologues or fragments of said integrin or subunit α11, and a polynucleotide and a oligonucleotide coding for said integrin subunit α11.

A method of gene therapy, whereby a vector comprising a polynucleotide or oligonucleotide coding for a subunit α11 of an integrin heterodimer, or for homologues or fragments thereof, which polynucleotide or oligonucleotide comprises essentially the nucleotide sequence shown in SEQ ID NO: 1 or parts thereof, and optionally a second vector comprising a polynucleotide or oligonucleotide coding for a subunit β of said integrin heterodimer, is administered to a subject suffering from pathological conditions involving said subunit α11.

A method of using binding entities having the capability of binding specifically to binding sites of a integrin subunit α11 comprising substantially the amino acid sequence shown in SEQ ID No. 1, or of an integrin heterodimer comprising said subunit α11 and a subunit β, or to homologues or fragments thereof, for promoting adhesion of cells.

A method of using an integrin heterodimer comprising an integrin subunit α11 and a subunit β, or the subunit α11 thereof, or homologues or fragments of said integrin or subunit α11, as a target for anti-adhesive drugs or molecules in tissues where adhesion impairs the function of the tissue.

A method of in vitro detecting the presence of integrin binding entities, comprising interaction of an integrin heterodimer comprising a subunit α11 and a sub-unit β, or the subunit α11 thereof, or homologues or fragments of said integrin or subunit, with a sample, thereby causing said integrin, subunit α11, or homologue or fragment thereof, to modulate the binding to its natural ligand or other integrin binding proteins present in said sample.

A method of in vitro studying consequences of the interaction of a human heterodimer integrin comprising a subunit α11 and a subunit β, or the subunit α11 thereof, or homologues or fragments of said integrin or subunit, with an integrin binding entity and thereby initiate a cellular reaction. In one embodiment of this method, the consequences of said interactions are measured as alterations in cellular functions.

A method of using a polynucleotide or oligonucleotide encoding an integrin subunit α11 or homologues or fragments thereof as a target molecule.

One embodiment of this method comprises hybridising a polynucleotide or oligonucleotide to the DNA or RNA encoding the integrin subunit α11 or homologue or fragment thereof, which polynucleotide or oligonucleotide fails to hybridise to a polynucleotide or oligonucleotide encoding an integrin subunit α10.

A method of using binding entities having the capability of binding specifically to an integrin subunit α10 comprising the amino acid sequence shown in SEQ ID No. 1 or SEQ ID No. 2, or an integrin heterodimer comprising said subunit α10 and a subunit β, or to homologues or fragments thereof having similar biological activity, for promoting adhesion of chondrocytes and/or osteoblasts to surfaces of implants to stimulate osseointegration.

A method of using an integrin heterodimer comprising an integrin subunit α11 and a subunit β, or the subunit α10 thereof, or homologues or fragments of said integrin or subunit α10, as a target for anti-adhesive drugs or molecules in tendon, ligament, skeletal muscle or other tissues where adhesion impairs the function of the tissue.

A method of stimulating, inhibiting or blocking the formation of cartilage or bone, comprising administration to a subject a suitable amount of a pharmaceutical agent or an antibody which is capable of using an integrin heterodimer comprising a subunit α11 and a sub-unit β, or the subunit α11 thereof, or homologues or fragments of said integrin or subunit α11, as a target molecule.

EXPERIMENTAL PROCEDURES

Cell Cultures

The human fetal myoblast/myotube cultures were derived from clone G6 originating from a thigh muscle of a 73-day old aborted fetus ((39); referred to as G6 hereafter). Cultures of G6 and 2.5 years postnatal human satellite cells XXVI, a gift from Dr. Helen Blau (Stanford University, CA), were grown as reported earlier (39). Human rhabdomyosarcoma cell lines RD (ATCC No. CCL-136) and A204 (ATCC No. CRL-7900) were grown in DMEM (Swedish Agricultural University, Uppsala) supplemented with 10% fetal calf serum.

RNA Isolation and cDNA Synthesis

Total RNA from G6 and XXVI myoblasts, the same cells differentiated for 3 or 7 days, and RD and A204 cell lines, was isolated using the RNeasy Midi kit (Qiagen) according to the manufacturer's instructions. Poly-A RNA was extracted from total RNA of G6 and XXVI cells using Dynabeads mRNA DIRECT kit (DYNAL A.S., Norway).

PCR Based Cloning and Generation of Human α11 Probes

First strand cDNA was generated from 1 µg of G6 mRNA using a reverse transcription PCR-kit (Perkin-Elmer). Advantage cDNA Polymerase Mix (Clontech) was used in PCR amplifications using two different pairs of primers: (1) 5' ACG GGA GAC GTG TAC AAG TG 3' (forward), 5'-AAA GTG CTG AAC CTC CAC CC-3' (reverse) and (2) 5'-CAC CAT CCA CCA GGC TAT GC-3' (forward), 5'-TTA GCG TTC CGT TAT AAA CA-3' (reverse). The PCR conditions were: 94° C., 4 min. ("hot start"); 94° C., 30 s; 55° C., 30 s; and 72° C., 1 min., for 25 cycles. Two products, named PCR1 and PCR2, were obtained (FIG. 1), subcloned into the plasmid vector TA (Invitrogen), and sequenced. A single product of 1.4 kb in size, named PCR 3 (FIG. 1), was amplified using primers 1 (forward) and 2 (reverse), and human heart Marathon-Ready cDNA (Clontech) as template. Annealing temperatures in the applied touch-down program were: 68° C., 1 min., 5 cycles; 65° C., 1 min., 5 cycles; 60° C., 1 min, 25 cycles. Other steps were as described above. After the final cycle the reactions were extended for additional 7 min. at 72° C. followed by a hold step at 4° C. To obtain a sequence covering the 5' end, Rapid Amplification of cDNA Ends (RACE) was employed according to the manufacturer's instructions (Marathon cDNA Amplification kit, Clontech) using cDNA prepared from G6 mRNA and the gene specific antisense primer: 5'-CTT GGA GAA CCT GAA GTT GGA GTT GAC-3'. Amplification was carried out applying the "touch-down" program (see above). To identify relevant products, 10 µl of each RACE product was resolved on 1% agarose gel and subjected to Southern blot analysis as described previously (40). PCR2 (see above) was labeled with [α-$^{32}$P]dCTP (Amersham Pharmacia Biotech, Sweden) using the RedyPrimeII DNA labeling system (Amersham Pharmacia Biotech, UK), and used as a hybridization probe. One specific signal was detected. Corresponding cDNA was purified (Gel Extraction kit, Quagen), cloned into the TA vector and sequenced (see FIG. 1).

Screening of cDNA Libraries

A λZAP custom made G6 cDNA library (Stratagene, USA) was screened with PCR2 (see above) as a probe. The screening procedure (carried out as described in (40)) resulted in two clones representing the 5' non-coding region and the beginning of the coding part of integrin α11 (FIG. 1). To obtain an additional sequence, a human uterus 5'-stretch λgt11 cDNA library (Clontech) was screened with a mixture of PCR1 and PCR2 as probes. The probes were labeled with [α-$^{32}$P]dCTP using the Ready-To-Go DNA labeling beads (Amersham Pharmacia Biotech, Sweden). Three clones (1.1-1.3 in FIG. 1) representing parts of α11 cDNA, were obtained. Rescreening of the human uterus 5'-stretch λgt11 cDNA library with the probe λ290 (corresponding to 2183-2473 in FIG. 1) yielded three more clones (2.1-2.3, FIG. 1) covering the rest of α11 cDNA. Positive clones were plaque purified, the phage DNA isolated using the Lambda Midi kit (Qiagen) and then sub-cloned into the Bluescript SK or pUC19 plasmid vectors before sequencing.

Northern Hybridization

A filter containing 6 µg of the poly-A RNA from G6 and XXVI cells and 10 µg of the total RNA from RD and A204 cell lines, and a Human Multiple Tissue Northern Blot containing poly-A RNA from adult human tissues (Clontech), were hybridized at 68° C. in ExpressHyb solution (Clontech) with probes labeled as described above. The probes used were PCR1, PCR2, cDNA clone 1.3 (FIG. 1), 3RA (1.8 kb cDNA specific for human integrin α1 mRNA, a generous gift from E. E. Marcantonio (Columbia University, New York), a 1.1 kb cDNA clone recognizing human G3PHD mRNA and a 1.8 kb cDNA clone recognizing human β-actin (both from Clontech).

cDNA Sequencing and Sequence Analysis

All PCR fragments and cDNA clones were sequenced on both strands either manually (29) or using ABI 310 Genetic Analyzer automatic sequencer. Sequences were analyzed with the aid of MacVector™ 6.0, DNA Star, Faktura™NEW 1.2.0, and Sequence Navigator 1.0.1 software programs. A distance tree of all I-domain containing integrin a subunits was assembled using SEAVIEW and PHYLO-WIN softwares (41). Percent similarity between every two members in the I-domain integrin subfamily was calculated by a formula I=(1−D)×100, where "I" is identity and "D" is distance.

Antibodies

A polyclonal antiserum (α11 cyt) was produced against the peptide CRREPGLDPTPKVLE from the integrin α11 cytoplasmic domain. Peptide synthesis and conjugation to Keyhole limpet hemocyanin, immunization of rabbits and affinity purification was performed at Innovagen AB (Lund, Sweden). The monoclonal antibody Mab 13 against integrin β1 was obtained from S. K. Akiyama (NIEHS, NIH). Monoclonal antibodies to integrin α1 (clone FB12, sold as MAB 1973) and integrin α2 (clone BHA2.1 sold as Mab 1998) were both obtained from Chemicon, Temecula, Calif. The monoclonal antibody to vinculin (clone hVIN-1) was from Sigma (Saint Louis, Mo., USA). Secondary fluorescent antibodies (CY3™-coupled goat-anti rabbit IgG and FITCcoupled goat anti-mouse IgG of multiple labeling grade) were from Jackson ImmunoResearch Laboratories, Inc. (West Grove, Pa., USA).

Immunoprecipitation and SDS-PAGE

G6 and XXVI cells were labeled with [$^{35}$S] cysteine/methionine and subjected to immunoprecipitation and SDS-PAGE as reported previously (38). The two-step procedure used to dissociate integrin heterodimers was carried out as follows. After incubation of samples with β1 antibody and capture with GammaBind G Sepharose (Amersham Pharmacia Biotech, Uppsala, Sweden), 100 µl of 1% SDS was added to the washed beads which were then boiled for 5 minutes. 10 mM Tris-HCl, pH 7.4, 0.15 M NaCl and 1% Triton X-100 was added to a final volume of 1 ml and the lysate was incubated with GammaBind G Sepharose for 1 hour. The incubation with GammaBind G was performed in order to ensure that no reactive β1 antibodies remained. After removal of GammaBind G Sepharose, α11 integrin antibody was added for additional 2 hours, followed by capture with protein A Sepharose (Amersham Pharmacia Biotech) and boiling in SDS-PAGE sample buffer.

Chromosomal Localization

Chromosomal localization of the human integrin α11 was performed by using a combination of FISH (Fluorescent In Situ Hybridization) technique and DAPI (4',6-diamidino-2-phenylindole) banding essentially as described earlier (42). As a hybridization probe, the 1.4 kb RT-PCR product PCR3 was used.

Surface Iodination and Affinity Chromatography

Cultured XXVI cells were surface iodinated as described (38). Labeled cells were solubilized in 1 ml of solubilization buffer (10 mM Tris-HCl pH 7.4, 15 mM NaCl, 1% Triton X-100, 1 mM MgCl$_2$, 1 mM CaCl$_2$, 1 mM MnCl$_2$), centrifuged at 14000 g for 20 min., and soluble membrane proteins were applied to a collagen type I Sepharose (bovine collagen type I from Vitrogen (Collagen Corp., Palo Alto) coupled to CNBr-activated Sepharose CL-4B at 3 mg/ml gel as described (14)), equilibrated in solubilization buffer. Following a one hour incubation the column was washed extensively with buffer A (10 mM Tris-HCl pH 7.4, 50 mM NaCl, 1 mM MnCl$_2$, 0.1% Triton X-100) and by 10 column volumes of buffer A without NaCl. Bound proteins were eluted with 20 mM EDTA, 10 mM Tris-HCl pH 7.4, 0.1% Triton X-100. Peak fractions were pooled and concentrated by immunoprecipitation with β1 integrin and α11 integrin antibodies as described under Immunoprecipitation and SDS-PAGE. Eluted frations and captured proteins were analyzed on 7.5% SDS-PAGE gels followed by autoradiography.

Indirect Immunofluorescence

Cells cultured on coverslips were washed in serumfree medium and fixed for 8 min. in acetone at −20° C. Nonspecific binding sites were blocked by incubating with 10% goat serum diluted in phosphate buffered saline. In the double immunofluorescence staining protocol, primary antibodies (anti-α11 cyt (rabbit antibody) and anti-vinculin (mouse antibody)) were simultaneously incubated with fixed cells for 1.5 hours at +37° C. Specifically bound antibodies were detected using anti-rabbit Cy3 IgG and anti-mouse FITC IgG. Stained cells were mounted in Vectashield™ mounting medium (Vector Laboratories, Inc., Burlingame, Calif., USA) and visualized and photographed under a Zeiss light microscipe equipped with optics for observing fluorescence.

RESULTS AND DISCUSSION cDNA Cloning of a Novel Integrin α-Chain

In order to determine the nature of the integrin chain that we had previously characterized on human fetal muscle cells and named αmt (38), a number of approaches were used. Applying PCR with mRNA from fetal muscle cells as template together with degenerate primers to conserved regions of integrin α subunits (43) we amplified cDNA for α1, α4, α5, α6 and αv integrin chains (data not shown), but failed to amplify the novel integrin. However, while searching through the literature we came across two integrin sequences obtained in a subtractive hybridization protocol comparing human primary myoblasts with the rhabdomyosarcoma cell line RD (44). After having confirmed that these sequences could be amplified by PCR from human fetal G6 myoblast cDNA, PCR was performed assuming that these sequences were derived from the same transcript. In this manner a 1.4 kb cDNA fragment with integrin-like sequence was obtained. Screening of a human fetal myoblast cDNA library and 5' RACE yielded additional 5' sequence. We determined the mRNA expression pattern in a number of human tissues (see below) and observed a high mRNA expression in the uterus. Screening of a uterus cDNA library resulted in the identification of the complete open reading frame. A schematic illustration of the cloning strategy is shown in FIG. 1.

cDNA Sequence and Predicted Amino Acid Sequence of α11 Integrin Chain

By sequence analysis of cDNA clones and 5' RACE products we obtained a continuous sequence of 3983 nucleotides (nt) composed of 90 nt 5' non-coding sequence, 3564 nt open reading frame, and 326 nt 3' non-coding sequence. Translation of the sequence predicts an integrin α-chain like precursor of 1188 amino acids including a 22 amino acid long signal peptide (FIG. 2, GenBank accession No. AF137378). The mature 1166 amino acid long peptide is larger than any other currently identified integrin α-chain (the closest being αE, composed of 1160 amino acids (45). The 1119 amino acid long predicted extracellular domain contains 7 FGGAP repeats in the amino-terminal end with an inserted I-domain between repeats 2 and 3. The I-domain consists of 195 amino acids and includes a conserved MIDAS motif. In addition to the metal chelating site in the I-domain, three additional potential divalent cation binding motifs with the consensus sequence DXD/NXDXXXD are present in repeats 5-7. A total of 20 cysteines are located in the extracellular domain. Of these, 16 are conserved in the most closely related integrin α10 and α1 chains and they may contribute to intramolecular disulphide bonds. The two non-conserved cysteines found at positions Cys 606 and Cys 988 most likely represent free unpaired cysteines while the two non-conserved cysteines Cys 806 and Cys 817 may pair to form a disulphide bond. Mapping of the cysteines in the suggested β-propeller structure shows that the first three disulphide bonds are likely to stabilize blades one and two of the β-propeller whereas the remaining bonds are found outside the propeller region, in the stalk region towards the transmembrane domain. 16 potentional N-glycosylation sites are present in α11. A search for sequence motifs reveals the presence of a 22 amino acid leucine zipper motif starting at position 951, and a 17 amino acid sequence starting at position 1082, which is similar to sequences found in G-protein coupled receptors. These sequences might represent functional domains of importance for protein-protein interactions.

The transmembrane region (amino acids 1142-1164) is 23 amino acids long and is followed by a cytoplasmic tail of 24 amino acids. The cytoplasmic tail contains the sequence (SEQ ID No. 4) GFFRS instead of the conserved GFFKR sequence (SEQ ID No. 5), found in all other α8-α10. It will be interesting to determine the importance of this sequence in defining the cytoplasmic domain as well as its possible ability to bind calreticulin and other intra-cellular components.

Comparison of Integrin α11 Chain with Other Integrin α chains

Figure 3:
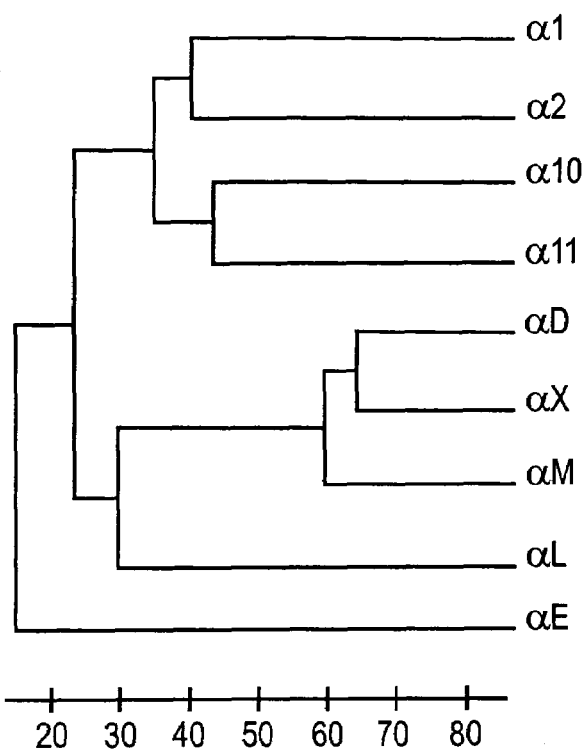

Alignment of the predicted α11 integrin amino acid sequence with other integrin sequences shows the highest overall identity with α10 (42% identity), α1 (37% identity), and α2 (35% identity), followed by the remaining I-domain containing integrin subunits. Of the non I-domain containing integrins, α4 and α9 are the most similar to α11. A distance tree shows that α10 and α11 form a separate branch from the most closely related α1 and α2 integrin chains (FIG. 3). The similarity with other integrins is particularly high in the N-terminal β-propeller part but lower in the stalk region. Comparison of α1 integrin with α2 integrin has pointed to the presence of a 38-residue insert in the β-propeller region of α1 integrin chain (15). Like α1 chain, α11 also contains inserted amino acids not present in the other I-domain containing integrin chains. however, in the α11 chain these are found within the stalk region at amino acids 804-826. The exact border of the predicted insertion varies depending on the alignment method and the parameters chosen, but is predicted to span at least 22 amino acids. The insert shows no significant similarity to other integrin sequences and contains two cysteines likely to form a disulphide bond (see FIG. 2). We do not believe that the predicted inserted sequence represents a cloning artifact since it is present in three independently analysed clones. Other examples of non I-domain inserted sequences are found in the Drosophila αPS2 chain, where developmentally regulated splicing in the ligand binding region modulates ligand affinity (46). In α7 integrin chain, splicing in the extracellular domain between predicted blades 2 and 3 in the β-propeller generates X1 and X2 variants, affecting the binding to laminin-1 in a cell-specific manner (47). In the more closely related α1 integrin chain the 38 extra amino acids are present in a position that is predicted to be in the beginning of the sixth blade of the 7-bladed propeller. So far there is no evidence that the extra amino acids in either α1 or α11 arise by alternative splicing. In α11 the predicted inserted region is outside the β-propeller and most likely does not directly affect ligand binding, but might instead be involved in modifying protein-protein interactions or be important for outside-in or inside-out signalling. In this regard it is interesting to note that tetraspan proteins by binding to the stalk region of certain integrin α-chains can recruit PI-4 kinase and protein kinase C to integrin complexes (48). Likewise the extracellular membrane-proximal parts of certain integrin α-chains have been shown to be involved in Shc-mediated integrin signalling (49).

Analysis of sequences identified during screening for genes upregulated during tadpole regression revealed a partial sequence, which at the time was reported to show the highest similarity to integrin α1 (41% identity) (50). This sequence, when translated (amino acids 1-116), shows 71% identity to human α11 and thus most likely represents the *Xenopus* orthologue of α11 rather than that of the α1. These data suggest that α11 is well conserved during evolution.

Chromosomal Localization of the Integrin α11 Gene

Figure 4A:
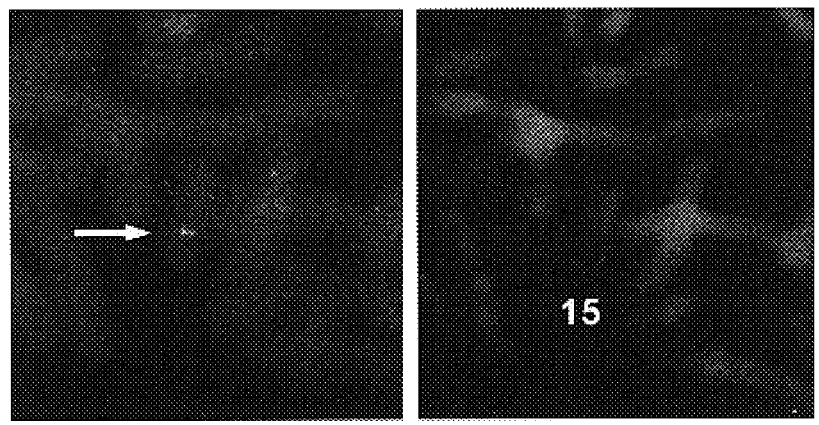
Figure 4B:
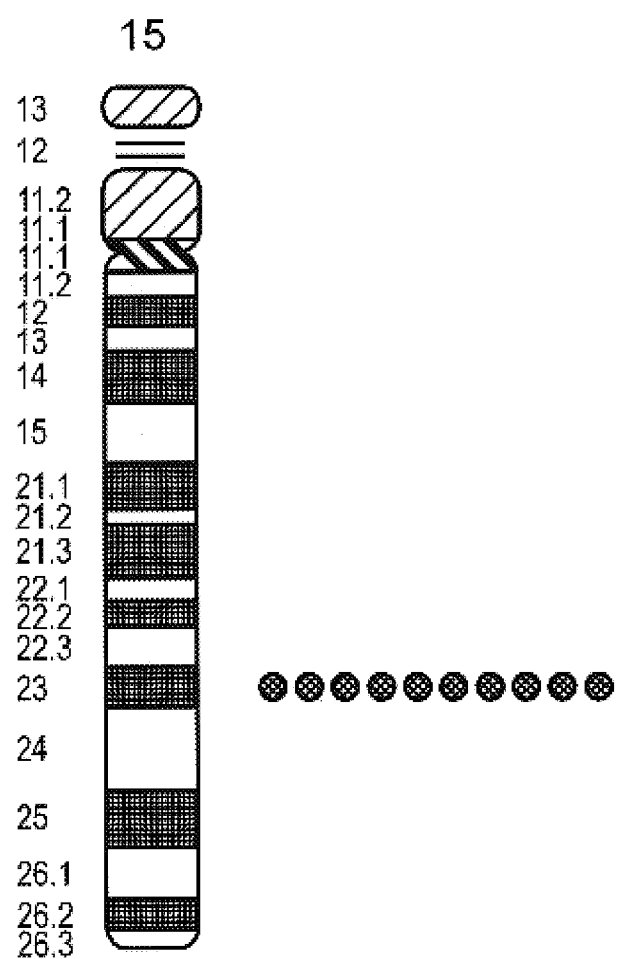

A fluorescent cDNA probe was used for in situ hybridization on metaphase chromosome spreads. The analysis shows that the integrin α11 gene (ITGA11) is located on chromosome 15q23 (FIG. 4). The genes for I-domain containing integrins α1 and α2 are both present on chromosome 5 (51, 52), just as the genes for the closely related β2 integrin associated α-chains all map to chromosome 16 (53). Interestingly, the α11 gene and the closely related α1 and α2 genes, map to different chromosomes. It will be of evolutionary interest to determine the chromosomal localization of the integrin α10 gene. Curiously, a form of Bardet-Biedl syndrome characterized by retinitis pigmentosa, polydactyl), obesity, hypogenitalism, mental retardation, and renal anomalies maps to 15q22-23 (54). Future studies will clarify a possible linkage of ITGA11 to Bardet-Biedl syndrome.

Expression Pattern of α11 mRNA in Adult Tissues

Figure 5:
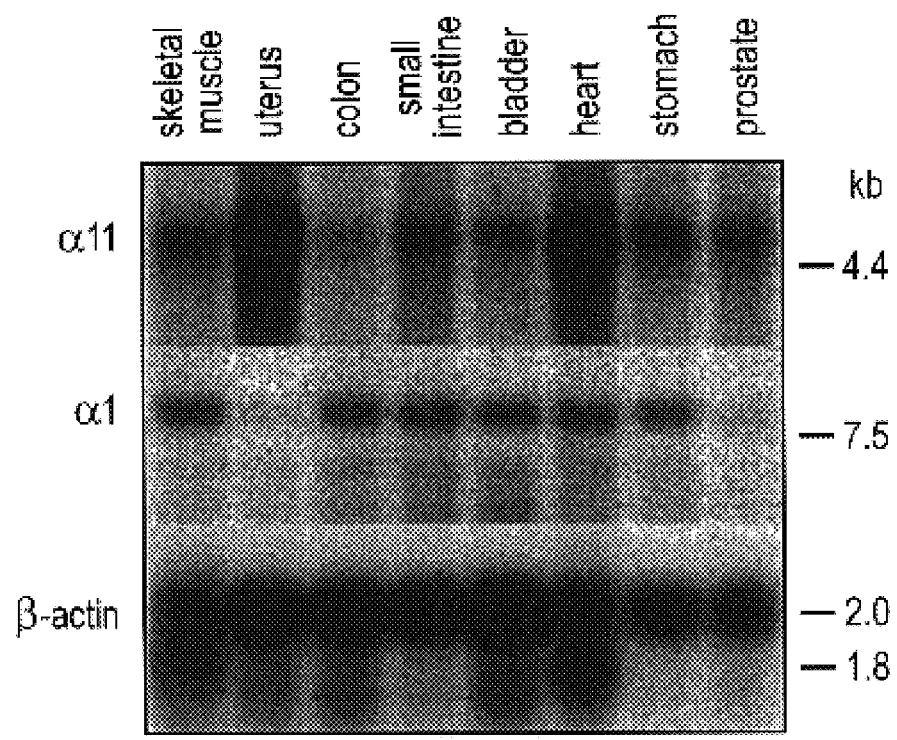

Northern blot analysis of mRNA from various adult human tissues shows the highest level of expression of α11 in adult human uterus. A strong signal is also noted in heart, while intermediate levels of α11 mRNA are present in skeletal muscle and intermediate to low levels in other adult tissues tested (FIG. 5 and data not shown). For a comparison, the same blot was probed for the closely related α1 integrin mRNA (FIG. 5). A striking difference in the expression levels of α1 and α11 was observed in the smooth muscle rich uterus, which appears to lack al. Immunohistochemical analysis and in situ hybridizations will elucidate the detailed distribution of α11 protein and mRNA in muscle and other tissues. Neither α1 (33) nor α2 (55) are present in muscle fibers, and the distribution of α10 in skeletal muscle tissues is not known (5). Hence, no I-domain containing integrin has so far been reported to be expressed in the skeletal muscle sarcolemma. Recently the gene for α1 integrin was inactivated in mice, resulting in mice with an apparently normal phenotype (56). More careful analysis revealed a phenotype characterized by a hypocellular skin (57) and aberrant regulation of collagen synthesis (58). It will be interesting to compare sites of overlapping expression between α1, α2 and α10 integrins, and use reagents to α10 and α11 to examine possible funcional compensatory mechanisms in α1 integrin-deficient mice.

Biochemical Characterization of α11 Protein

Following the cloning of the full-length α11 integrin cDNA it was essential to determine if the predicted amino acid sequence was identical to the novel uncleaved β1 integrin-associated α-chain that we had previously noted to be upregulated during in vitro differentiation of human myoblasts (38). To answer this question we raised antibodies to the cytoplasmic tail of the integrin α11 chain. Immunoprecipitation from the human satellite cells showed that the antibodies precipitated a 145 kDa α11 band associated with a 115 kDa β1 band (FIG. 6, panel A) in SDS-PAGE under non-reducing conditions. Under reducing conditions the α11 band migrated as 155 kDa (see FIG. 6, panel B). From the translated amino acid sequence an Mr of 133 400 is predicted for the α11 chain. Taking the 16 potential glycosylation sites into account this fits well with the observed 155 kDa band in SDS-PAGE. Under non-reducing conditions the 145 kDa band is distinctly larger than α2 (FIG. 6, panel A) and α10 integrin chains which co-migrate as 140 kDa bands and α11 migrates well below the 180 kDa integrin α1 band. The α2 (59) and α10 (5) chains both contain 10 potentional glycosylation sites whereas α1 contains 26 glycosylation sites (60). The intermediate size of α11 in SDS-PAGE compared with α1 and α2/α10 is thus most likely a result of differential glycosylation.

To show that α11 is associated with the β1 subunit a two-step immunoprecipitation procedure was performed. Integrins were first precipitated with a monoclonal antiβ1 integrin antibody and GammaBind G captured integrins were then dissociated by boiling in 1% SDS. In the second step, SDS was diluted tenfold and antibodies to α11 were added. As shown in FIG. 6 panel A antibodies to α11 immunoprecipitate only the 145 kDa band from the dissociated precipitate initially captured with β1 antibodies.

Induction of α11 mRNA and Protein During Myogenic Differentiation In Vitro

It has previously been determined that αmt is the major integrin α-chain that is up-regulated during myogenic differentiation on human fetal myoblasts in vitro (38). To compare α11 levels in myoblasts and myotubes, immuno-precipitates were analyzed from myoblast cultures in pro-liferation medium, and from parallel cultures allowed to differentiate and form myotubes in differentiation medium for 7 days. Immunoprecipitation with both β1 and α11 antibodies showed that α11, like αmt, is strongly up-regulated at the protein level in differentiation cultures of human fetal muscle cells and satellite cells (FIG. 6, panel B). To determine if the up-regulation occurs at the mRNA or protein level we analyzed all mRNA from different differentiation stages (day 1, day 3 and day 7) (FIG. 6, panel C). Already at day 3 in differentiation medium a strong up-regulation of α11 mRNA was noted, establishing that the up-regulation of α11 integrin protein occurs as a result of increased transcription or mRNA stability. Based on similar SDS-PAGE migration patterns, similar behavior under reducing conditions, association with β1 integrin chain, and up-regulation during in vitro differentiation of human fetal myoblasts, the present data show that α11 integrin is identical with αmt.

Analysis of mRNA from the two rhabdomyosarcoma cell lines RD and A204 (FIG. 6, panel C) did not provide evidence for the presence of α11 in either cell line. Based on the observed up-regulation of α11β1 in human fetal muscle cells and the presence of α11 message in adult muscle we suggest that α11 integrin might be involved in early steps of muscle formation and that it in adult muscle tissues may fulfill a stabilizing role. The α7 integrin subunit is a major β1-associated integrin chain in muscle, but genetic deletion of α7 leads to a fairly mild muscular dystrophy (30).

Ligand Binding Specificity of α11β1 Integrin

Figure 7A:
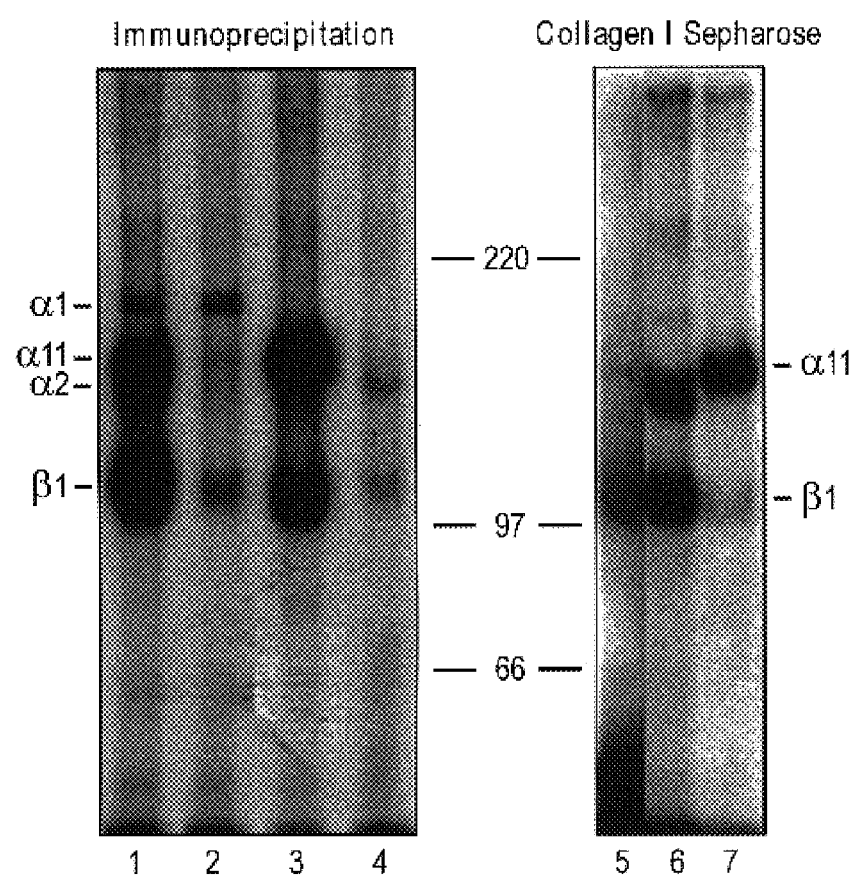
Figure 7B:
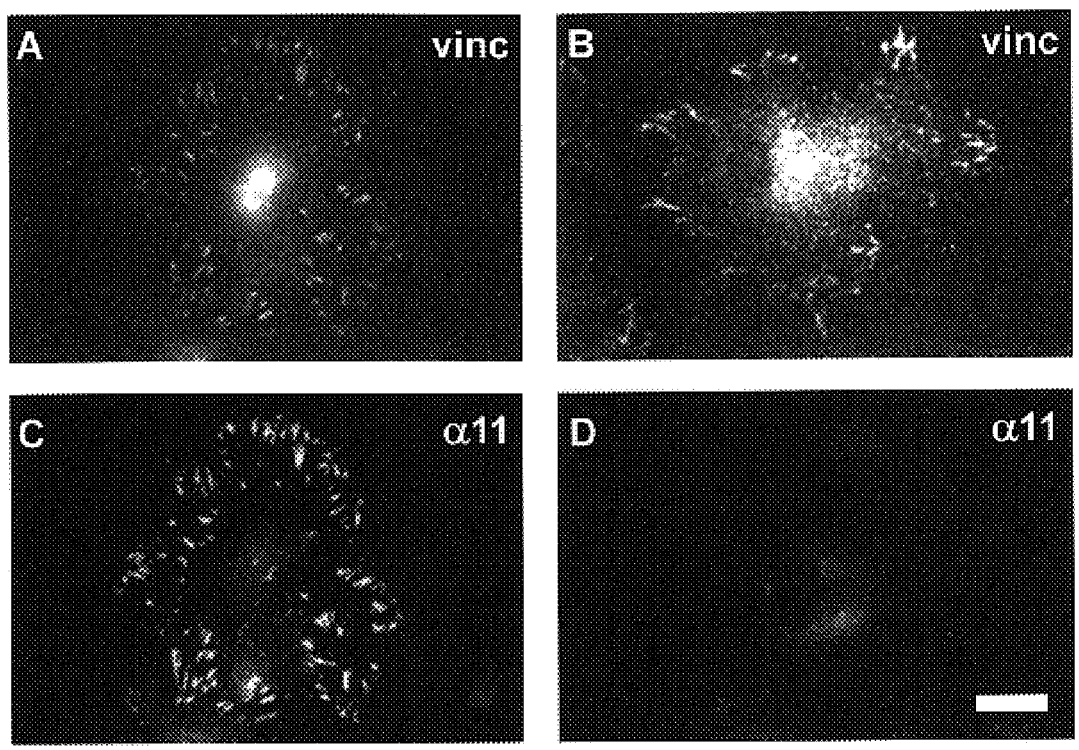

So far identified I-domain containing integrins of the β1 integrin subfamily all bind collagens (5, 15, 59). For α1 and α2 this binding capacity has been shown to reside within the I-domain (17, 18). To determine if α11β1 also binds collagen we performed collagen type I Sepharose chromatography of membrane proteins from surfaceiodinated XXVI satellite cells. Direct analysis of the EDTA eluate revealed weak bands corresponding to the positions of α1, α2, α11 and β1 in parallel immunoprecipitations (FIG. 7, panel 1). The EDTA eluate was concentrated by immunoprecipitation with β1 and α11 antibodies. As shown in FIG. 7, a prominent α11 band is present in the collagen I Sepharose eluate. The relatively weak β1 band in the proteins captured with α11 antibodies indicates that the α11β1 heterodimer partly dissociates in the presence of EDTA. To visualize the interaction of α11β1 integrin with collagen I in intact cells, myogenic cells expressing α11β1 were trypsinized and plated on collagen and fibronectin for 1 hour. The ability to form focal contacts was investigated by double immunofluorescence staining for α11-chain and vinculin. As seen in panel 2 of FIG. 7 α11 localizes to vinculin positive focal contacts on collagen but not on fibronectin. Binding studies with α11 I-domain expressed as a bacterial GST-fusion protein also confirmed a specific affinity for collagen I (unpublished M. Höök, R. Rich, R. Owens). Stable transfections of α11 cDNA into cells with various integrin backgrounds will allow a more detailed study of α11β1 interactions with different collagen, and possibly also laminin, isoforms. Combined with in vivo distribution studies of α11β1 this is likely to yield valuable information regarding the in vivo ligands for α11β1 in different tissues.

α11 Integrin Protein Distribution in Human Embryo

Morphologically normal human embryos (aged from 4 to 8 post-ovulatory weeks) were obtained from legal abortions induced by Mifepristone (RU486) at Hopital Broussais in Paris. All procedures were approved by the Ethical Committee of Saint-Vincent de Paul Hospital in Paris.

Each sample was first examined macroscopically during dissection under a stereo-microscope. The development stage of the embryos was determined using established criteria. Tissues were collected shortly after delivery and frozen within the first 24 h post mortem on dry ice and stored at −80° C. until used. Seven micron-thick cryostat sections were mounted on slides previously coated with a 2% 3-aminopropyl-triethoxysilane solution in acetone. The cryosection was left unfixed prior to blocking of non-specific binding sites with 10% goat serum diluted in phosphate buffered saline. For immunofluorscence, the section was incubated with α11 antibodies 1.5 h at +37° C. Specifically bound antibodies were detected using goat anti-rabbit Cy3 IgG (Jackson Immunoresearch). The stained tissue section was mounted in Vectashield™ mounting medium (Vector Laboratories Inc.) and visualized and photographed under a Zeiss ligth microscope equipped with optics for observing fluorescence.

Figure 8:
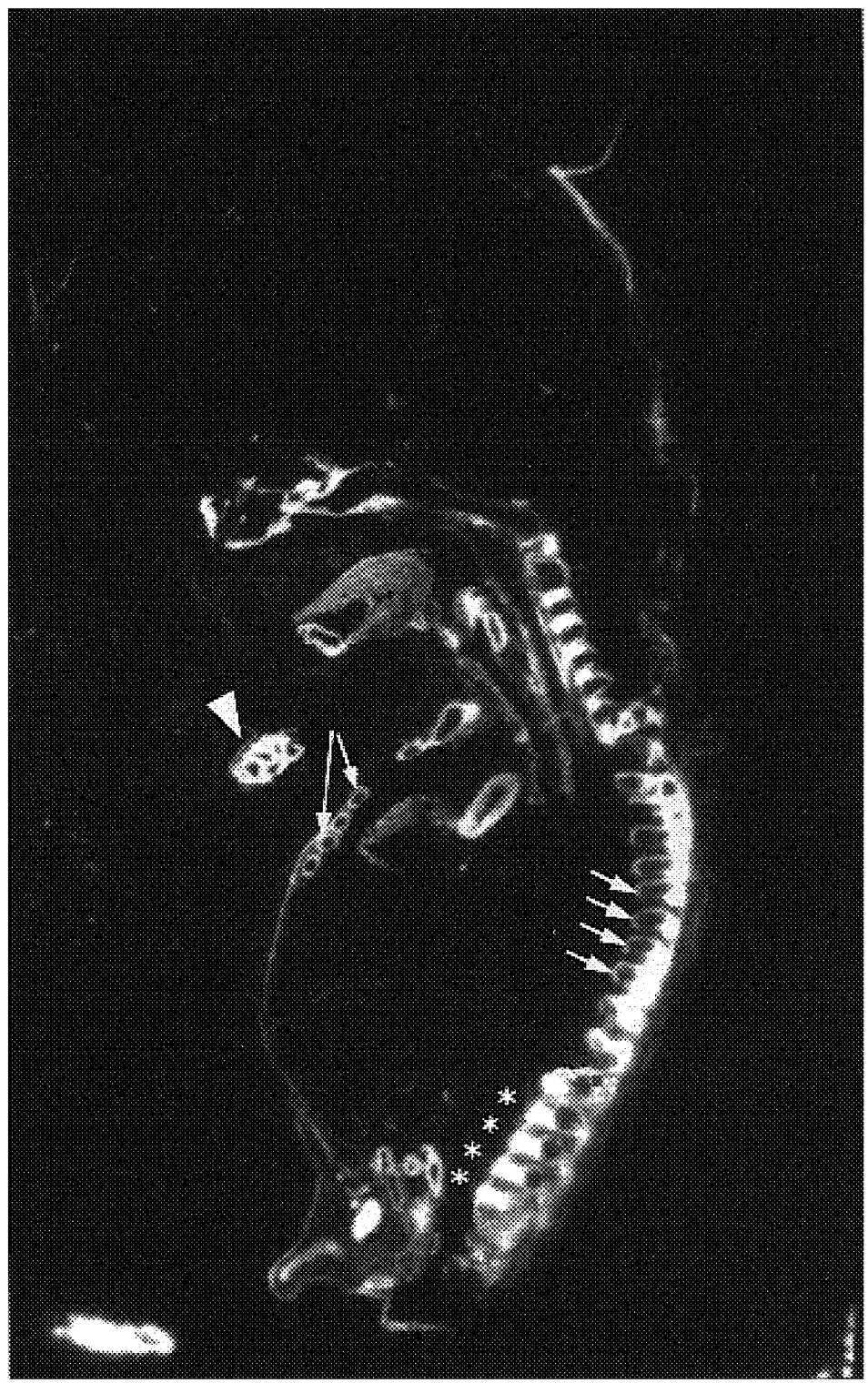

The results obtained are shown in FIG. 8. High levels of α11 protein were noted around vertebrae (arrows), in intervertebrae disc (asterisks), around ribs (thin arrows) and around forming cartilage in the forelimb (arrowhead).

REFERENCES

1. Hynes, R. O. (1992) Cell 69, 11-25
2. Adams, J., and Watt, F. M. (1993) Development 117, 1183-1198
3. Sastry, S. K., and Horwitz, A. F. (1996) Dev. Biol. 180, 455-467
4. Gullberg, D., Tiger, C.-F, Lohikangas, L., and Velling, T. (1998) Front. Biosci. 3, 1028-1039
5. Camper, L., Hellman, U., and Lundgren-Akerlund, E. (1998) J. Biol. Chem. 273, 20383-20389
6. Aumailley, M., Gerl, M., Sonnenberg, A., Deutzmann, R., and Timpl, R. (1990) FEBR Lett 262, 82-86
7. Pfaff, M., Aumailly, M., Specks, U., Knolle, J., Zerwes, H. G., and Timpl, R. (1993) Exp. Cell Res. 206, 167-176
8. Davis, G. E. (1992) Biochem. Biophys. Res. Commun. 182, 1025-1031
9. Goodman, S. L., Aumailly, M., and von der Mark, H. (1991) J. Cell Biol. 113, 931-941
10. Dickeson, S. K., and Santoro, S. A. (1998) Cell. Mol. Life Sci. 54, 556-566
11. Takada, Y., Kamata, T., Irie, A., Puzon-McLaughlin, W., and Zhang, X. P. (1997) Matrix Biol. 16, 143-151
12. Colombatti, A., Bonaldo, P., and Doliana, R. (1993) Matrix 13, 297-306
13. Lee, J.-O., Rieu, P., Arnaout, M. A., and Liddington, R. C. (1995) Cell 80, 631-635
14. Gullberg, D., Turner, D. C., Borg, T. K., Terracio, L., and Rubin, K. (1990) Exp. Cell Res. 190, 254-264
15. Ignatius, M. J., Large, T. H., Houde, M., Tawil, J. W., Barton, A., Esch, F., Carbonetto, S., and Reichardt, L. F. (1990) J. Cell Biol. 111, 709-720
16. Dickeson, S. K., Walsh, J. J., and Santoro, S. A. (1997) J. Biol. Chem. 272, 7661-7668
17. Calderwood, D. A., Tuckwell, D. S., Eble, J., Kuhn, K., and Humphries, M. J. (1997) J. Biol. Chem. 272, 12311-12317
18. Tuckwell, D., Calderwood, D. A., Green, L. J., and Humphries, M. J. (1995) J. Cell Sci. 108, 1629-1637
19. Tuckwell, D. S., Reid, K. B. M., Barnes, M. J., and Humphries, M. J. (1996) Eur. J. Biochem. 241, 732-739
20. King, S. L., Kamata, T., Cunningham, J. A., Emsley, J., Liddington, R. C., Takada, Y., and Bergelson, J. M. (1997) J. Biol. Chem. 272, 28518-28522
21. Springer, T. A. (1997) Proc. Natl. Acad. Sci. USA 94, 65-72
22. Huang, C., and Springer, T. A. (1997) Proc. Natl. Acad. Sci. USA 94, 3162-3167
23. Oxvig, C., and Springer, T. A. (1998) Proc. Natl. Acad. Sci. USA 95, 4870-4875
24. Huang, C., Lu, C., and Springer, T. A. (1997) Proc. Natl. Acad. Sci. USA 94, 3156-3161
25. Rojiani, M. V., Finlay, B. B., Gray, V., and Dedhar, S. (1991) Biochemistry 30, 9859-9866
26. Wright, T. F. (1960) J. Exp. Zool. 143, 77-99
27. MacKrell, A. J., Blumberg, B., Haynes, S. R., and Fessler, J. H. (1988) Proc. Natl. Acad. Sci. USA 85, 2633-2637
28. Bloor, J. A., and Brown, N. H. (1998) Genetics 148, 1127-1142
29. Gullberg, D., Fessler, L. I., and Fessler, J. H. (1994) Dev. Dynamics 199, 116-128
30. Mayer, U., Saher, G., Fassler, R., Bornemann, A., Echtermeyer, F., von der Mark, H., Miosge, N., Poschl, E., and von der Mark, K. (1997) Nat. Genet. 17, 318-323
31. Hayashi, Y. K., Chou, F.-L., Engvall, E., Ogawa, M., Matsuda, C., Hirabayashi, S., Yokochi, K., Ziober, B. L., Kramer, R. H., Kaufman, S. J., Ozawa, E., Goto, Y., Nonaka, I., Tsukahara, T., Wang, J.-Z., Hoffman, E. P., and Arahata, K. (1998) Nat. Genet. 19, 94-97
32. Song, W. K., Wang, W., Foster, R. F., Biesler, D. A., and Kaufman, S. J. (1992) J. Cell Biol. 117, 643-657
33. Martin, P. T., Kaufman, S. J., Kramer, R. H., and Sanes, J. R. (1996) Dev. Biol, 174, 125-139
34. Belkin, A., Zhidkova, N. I., Balzac, F., Altruda, F., Tomatis, D., Maier, A., Tarone, G., Koteliansky, V. E., and Burridge, K. (1996) J. Cell Biol. 132, 211-226
35. Miyagoe, Y., Hanaoka, K., Nonaka, I., Hayasaka, M., Nabeshima, Y., Arahata, K., Nabeshima, Y., and Takeda, S. (1997) FEBS Lett. 415, 33-39
36. Xu, H., Christmas, P., Wu, X. R., Wewer, U. M., and Engvall, E. (1994) Prox. Natl. Acad. Sci. USA 91, 5572-5576
37. Sunada, Y., Bernier, S. M., Kozak, C. A., Yamada, Y., and Campbell, K. P. (1994) J. Biol. Chem. 269, 13729-13732
38. Gullberg, D., Velling, T., Sjöberg, G., and Sejersen, T. (1995) Dev. Dyn. 204, 57-65
39. Jin, P., Farmer, K., Ringertz, N. R., and Sejersen, T. (1993) Differentiation 54, 47-54
40. Sambrook, J., Fritsch, E., and Maniatis, T. (1989) Molecular cloning: A Laboratory Manual, Second Edition Ed., Cold Spring Laboratory Press, NY
41. Galtier, N., Gouy, M., and Gautier, C., (1996) Comput. Appl. Biosci. 12, 543-548
42. Heng, H., Squire, J., and Tsui, L.-C (1992) Proc. Natl. Acad. Sci. USA 89, 9509-9513
43. Pytela, R., Suzuki, S., Breuss, J., Erle, D. J., and Sheppard, D. (1994) Methods Enzymol. 245, 420-451
44. Genini, M., Schwalbe, P., Scholl, F. A., and Schafer, B. W. (1996) Int. J. Cancer 66, 571-577

45. Shaw, S. K., Cepek, K. L., Murphy, E. A., Russel, G. J., Brenner, M. B., and Parker, C. M. (1994) J. Biol. Chem. 269, 6016-6025
46. Fogerty, F. J., Fessler, L. I., Bunch, T. A., Yaron, Y., Parker, C. G., Nelson, R. E., Brower, D. L., Gullberg, D., and Fessler, J. H. (1994) Development 120, 1747-1758
47. Ziober, B. L., Chen, Y., and Kramer, R. H. (1997) Mol. Biol. of the Cell 8, 1723-1734
48. Hemler, M. E. (1998) Curr. Opin. Cell Biol. 10, 578-585
49. Wary, K. K., Mainiero, F., Isakoff, S. J., Marcantonio, E. E., and Giancotto, F. G. (1996) Cell 87, 733-743
50. Brown, D. D., Wang, Z., Furlow, J. D., Kanamori, A., Schwartzman, R. A., Remo, B. F., and Pinder, A. (1996) Proc. Natl. Acad. Sci. USA 93, 1924-1929
51. Jaspers, M., Marynen, P., Aly, M. S., Cuppens, H., Hilliker, C., and Cassiman, J. J. (1991) Somat. Cell Mol. Genet. 17, 505-511
52. Seymour, A. B., Yanak, B. L., O'Brien, E. P., Rusiniak, M. E., Novak, E. K., Pinto, L. H., Swank, R. T., and Gorin, M. B. (1996) Genome Res. 6, 538-544
53. Wong, D. A., Davis, E. M., Le Beau, M., and Springer, T. A. (1996) Gene 171, 291-294
54. Bruford, E. A., Riise, R., Teague, P. W., Porter, K., Thomson, K. L., Moore, A. T., Jay, M., Warburg, M., Schinzel, A., Tommerup, N., Tornqvist, K., Rosenberg, T., Patton, M., Mansfield, D. C., and Wright, A. F. (1997) Genomics, 41, 93-99
55. Wu, J. E., and Santoro, S. A. (1994) Dev. Dyn. 199 (292-314)
56. Gardner, H., Kreidberg, J., Koteliansky, V., and Jaenisch, R. (1996) Dev. Biol. 175, 301-313
57. Pozzi, A., Wary, K. K., Giancotti, F. G., and Gardner, H. A. (1998) J. Cell Biol. 142, 587-594
58. Gardner, H., Broberg, A., Pozzi, A., Laato, M., and Heino, J. (1999) J. Cell Sci. 112, 263-272
59. Takada, Y., and Hemler, M. E. (1989) J. Cell Biol. 109, 397-407
60. Briesewitz, R., Epstein, M. R., and Marcantonio, E. E. (1993) J. Biol. Chem. 268, 2989-2996

FIGURE LEGENDS

FIG. 1. Schematic Organization of PCR Fragments and cDNA Clones Representing Different Parts of the Full Length Sequence of Integrin α11 Subunit A. Clones 1.1-1.3 and 2.1-2.3 are from the first and the second round of screening, respectively. Fragment 0.0 represents a 5' RACE product as well as a clone obtained from screening of the G6 library. PCR fragments 1-3 and a SacI fragment of a clone 1.3, λ290, are marked with thick lines. Names and positions of all the clones on a scheme are shown in tabulated form in B.

B. Names of the PCR-amplified fragments and cDNA clones shown in A are in the left column, and their positions in the full length cDNA of integrin α11 in the right column.

FIG. 2. Nucleotide and Dedued Amino Acid Sequence of the Human Integrin α11 Chain The putative signal peptide is underlined in bold, I-domain is boxed, potential N-linked glycosylation sites are marked with asterisks, cysteines are underlined, potential divalent cation binding motifs are double underlined and the transmembrane domain is underlined with dashes. A 22 amino acid insert is boxed in bold.

FIG. 3. A Distance Tree of the I-Domain Containing α-Integrin Subfamily Members

A tree was assembled based using ClustalW multiple alignment-based SEAVIEW and PHYLOWIN softwares. A scale at the bottom shows percent identity.

FIG. 4. Chromosome mapping of ITGA11 Gene by Fluorescent In Situ Hybridization (FISH)

A. Left panel shows the FISH signals on human chromosome 15; right panel shows the same mitotic figure stained with 4',6-diamino-2-phenylindole to identify human chromosome 15.

B. Diagram of FISH mapping result for the probe PCR3 based on a detailed analyses of 10 different images. Each dot represents the double FISH signals detected on human chromosome 15.

FIG. 5. Expression of Integrin α11 and α1 Subunit mRNAs in Adult Human Tissues

Integrin α11 mRNA and integrin α1 mRNA were analyzed on a membrane with RNA from various adult human tissues where mRNA loading was normalized with respect to β-actin. Probes used for hybridizations are marked on the left. Size of molecular weight standard is marked to the right. Note that the β-actin probe reacts with 2 kb β/γ actin transcripts and the muscle specific 1.8 kb α-actin message.

FIG. 6. Biochemical Characterization of Integrin α11 Chain and Upregulation of Corresponding Protein and mRNA in Myogenic Cells A. α11 associates with β1 integrin chain. Human XXVI and G6 muscle cells were metabolically labeled with [$^{35}$S] cysteine/methionine and integrins were immunoprecipitated with the indicated antibodies (β1, α2 and α11). Evidence for the association of integrin α11 with the β1 subunit obtained by treating proteins precipitated with anti-β1 antibodies with SDS followed by a second precipitation with α11 antibodies (ant-α11+SDS). Precipitated proteins were resolved on 7.5% SDS-PAGE gels in the absence of reducing agents, followed by fluorography.

B. Induction of Integrin α11 Upon Myogenic Differentiation In Vitro.

G6 muscle cells were metabolically labeled with [$^{35}$S] cysteine/methionine when growing in proliferation medium (mb-proliferating myoblasts) and after 7 days in differentiation medium) (mt-myotubes). Integrins were precipitated with antibodies to β1 and α11 and the precipitates were resolved on 7.5% SDS-PAGE gels both under non-reducing (UNREDUCED) and reducing (REDUCED) conditions. Lanes 1, 3, 5 and 7 are immunoprecipitations with the antibody to integrin β1, and lanes 2, 4, 6 and 8 with the antibody to integrin α11.

C. Upregulation of Integrin α11 mRNA in Differentiated Myogenic Cells.

mRNA was extracted from G6 and XXVI cells growing under proliferating (p) or differentiating (d) conditions for 3 days (d3) or 7 days (d7). Total RNA was isolated from RD and A204 cells. Following separation of RNA on agarose gel and transfer to the membrane, the filter was hybridized with probes to α11 integrin (α11) and glyceraldehyde-3-phosphate dehydrogenase (GAPDH). Size of bands in RNA standard (in kb) are marked to the right.

FIG. 7. Ligand Binding Properties of α11β1 Integrin Panel 1: Collagen Binding Integrins on XXVI Cells.

XXVI cells were surface iodinated and integrins were analyzed by immunoprecipitation and collagen I Sepharose affinity chromatography. Immunoprecipitation reveals the presence of β1 integrins (lane 1), α1β1 (lane 2), α11β1 (lane 3) and α2β1 (lane 4) at the surface of XXVI cells. EDTA eluted proteins bound to collagen I Sepharose contain weak band in the position of α1, α11, α2 and β1 integrin chains (lane 5). Immunoprecipitations with β1 integrin antibodies (lane 6) and α11 integrin antibodies (lane 7) confirm the presence of α11 and β1 in the EDTA eluate.

Panel 2: α11β1 Localizes to Focal Contacts on Collagen.

Indirect immunofluorescent visualization of vinculin (A, B) and α11 integrin chain (C, D) in human XXVI satellite cells seeded on collagen type I (A and C) and fibronectin (B and D). Note the localization of integrin α11 chain to focal contacts of cells allowed to attach to collagen and its complete absence on cells seeded on fibronectin. Vinculin is found in focal contacts on both substrates. A and C show the same cell double stained for both antigens. Scale bar is 20 μm.

FIG. 8. α11 Integrin Protein Distribution at 8 Weeks of Gestation.

Composite of immunohistochemical staining of sagital section of human embryo at 8 weeks of gestation. Note high levels of α11 protein around vetrebrae (arrows), in intervertebral disc (asterisks), around ribs (thin arrows) and around forming cartilage in the forelimb (arrowhead).

The invention claimed is:

1. A polypeptide comprising the extracellular domain of integrin subunit α11, wherein the extracellular domain of integrin subunit α11 consists of amino acids 23 to 1141 of SEQ ID NO:2, wherein said polypeptide is not amino acids 1 to 1188 of SEQ ID NO:2 or amino acids 23 to 1188 of SEQ ID NO:2.

2. A polypeptide comprising a fragment of the extracellular domain of integrin subunit α11, wherein the fragment consists of the I-domain of integrin subunit α11 from amino acids 159 to 355 of SEQ ID NO:2, wherein said polypeptide is not amino acids 1 to 1188 of SEQ ID NO:2 or amino acids 23 to 1188 of SEQ ID NO:2.

3. A polypeptide comprising a fragment of the extracellular domain of integrin subunit α11, wherein the fragment consists of amino acids 804 to 826 of SEQ ID NO:2, wherein said polypeptide is not amino acids 1 to 1188 of SEQ ID NO:2 or amino acids 23 to 1188 of SEQ ID NO:2.

4. A polypeptide comprising the cytoplasmic domain of integrin subunit α11, wherein the cytoplasmic domain of integrin subunit α11 consists of amino acids 1165 to 1188 of SEQ ID NO:2, wherein said polypeptide is not amino acids 1 to 1188 of SEQ ID NO:2 or amino acids 23 to 1188 of SEQ ID NO:2.

5. A polypeptide comprising the transmembrane domain of integrin subunit α11, wherein the transmembrane domain of integrin subunit α11 consists of amino acids 1142 to 1164 of SEQ ID NO:2, wherein said polypeptide is not amino acids 1 to 1188 of SEQ ID NO:2 or amino acids 23 to 1188 of SEQ ID NO:2.

6. A heterodimer comprising:
   (a) the polypeptide of claim 1; and
   (b) the integrin subunit β1.

7. The heterodimer of claim 6, wherein the extracellular domain of integrin subunit α11 is non-covalently associated with the integrin subunit β1.

* * * * *

UNITED STATES PATENT AND TRADEMARK OFFICE
CERTIFICATE OF CORRECTION

PATENT NO.         : 7,485,429 B1
APPLICATION NO.  : 09/980403
DATED              : February 3, 2009
INVENTOR(S)        : Donald Gullberg Page 1 of 1

It is certified that error appears in the above-identified patent and that said Letters Patent is hereby corrected as shown below:

On the cover page,

[*] Notice:   Subject to any disclaimer, the term of this patent is extended or adjusted under 35 USC 154(b) by (27) days Delete the phrase "by 27 days" and insert -- by 58 days --

Signed and Sealed this

Twenty-eighth Day of July, 2009

JOHN DOLL
*Acting Director of the United States Patent and Trademark Office*

```
                       SEQUENCE LISTING

<160> NUMBER OF SEQ ID NOS: 5

<210> SEQ ID NO 1
<211> LENGTH: 3983
<212> TYPE: DNA
<213> ORGANISM: human
<220> FEATURE:
<221> NAME/KEY: CDS
<222> LOCATION: (91)..(3654)

<400> SEQUENCE: 1
ggcacgaggc cgcgccgagg aggctgccgc tctggcttgc cagtccccg ccgccgctgc         60 acaccggacc cagccgccgt gccgcgggcc atg gac ctg ccc agg ggc ctg gtg        114
                                 Met Asp Leu Pro Arg Gly Leu Val
                                   1               5 gtg gcc tgg gcg ctc agc ctg tgg cca ggg ttc acg gac acc ttc aac         162
Val Ala Trp Ala Leu Ser Leu Trp Pro Gly Phe Thr Asp Thr Phe Asn
         10                  15                  20 atg gac acc agg aag ccc cgg gtc atc cct ggc tcc agg acc gcc ttc         210
Met Asp Thr Arg Lys Pro Arg Val Ile Pro Gly Ser Arg Thr Ala Phe
 25                  30                  35                  40 ttt ggc tac aca gtg cag cag cac gac atc agt ggc aat aag tgg ctg         258
Phe Gly Tyr Thr Val Gln Gln His Asp Ile Ser Gly Asn Lys Trp Leu
                     45                  50                  55 gtc gtg ggc gcc cca ctg gaa acc aat ggc tac cag aag acg gga gac         306
Val Val Gly Ala Pro Leu Glu Thr Asn Gly Tyr Gln Lys Thr Gly Asp
                 60                  65                  70 gtg tac aag tgt cca gtg atc cac ggg aac tgc acc aaa ctc aac ctg         354
Val Tyr Lys Cys Pro Val Ile His Gly Asn Cys Thr Lys Leu Asn Leu
             75                  80                  85 gga agg gtc acc ctg tcc aac gtg tcc gag cgg aaa gac aac atg cgc         402
Gly Arg Val Thr Leu Ser Asn Val Ser Glu Arg Lys Asp Asn Met Arg
         90                  95                 100 ctc ggc ctt agt ctc gcc acc aac ccc aag gac aac agc ttc ctg gcc         450
Leu Gly Leu Ser Leu Ala Thr Asn Pro Lys Asp Asn Ser Phe Leu Ala
105                 110                 115                 120 tgc agc ccc ctc tgg tct cat gag tgt ggg agc tcc tac tac acc aca         498
Cys Ser Pro Leu Trp Ser His Glu Cys Gly Ser Ser Tyr Tyr Thr Thr
                    125                 130                 135 ggg atg tgt tca aga gtc aac tcc aac ttc agg ttc tcc aag acc gtg         546
Gly Met Cys Ser Arg Val Asn Ser Asn Phe Arg Phe Ser Lys Thr Val
                140                 145                 150
```

```
gcc cca gct ctc caa agg tgc cag acc tac atg gac atc gtc att gtc      594
Ala Pro Ala Leu Gln Arg Cys Gln Thr Tyr Met Asp Ile Val Ile Val
        155                 160                 165 ctg gat ggc tcc aac agc atc tac ccc tgg gtg gag gtt cag cac ttc      642
Leu Asp Gly Ser Asn Ser Ile Tyr Pro Trp Val Glu Val Gln His Phe
170                 175                 180 ctc atc aac atc ctg aaa aag ttt tac att ggc cca ggg cag atc cag      690
Leu Ile Asn Ile Leu Lys Lys Phe Tyr Ile Gly Pro Gly Gln Ile Gln
185                 190                 195                 200 gtt gga gtt gtg cag tat ggc gaa gat gtg gtg cat gag ttt cac ctc      738
Val Gly Val Val Gln Tyr Gly Glu Asp Val Val His Glu Phe His Leu
                205                 210                 215 aac gac tac agg tct gta aaa gat gtg gtg gaa gct gcc agc cac att      786
Asn Asp Tyr Arg Ser Val Lys Asp Val Val Glu Ala Ala Ser His Ile
        220                 225                 230 gag cag aga gga gga aca gag acc cgg acg gca ttt ggc att gaa ttt      834
Glu Gln Arg Gly Gly Thr Glu Thr Arg Thr Ala Phe Gly Ile Glu Phe
    235                 240                 245 gca cgc tca gag gct ttc cag aag ggt gga agg aaa gga gcc aag aag      882
Ala Arg Ser Glu Ala Phe Gln Lys Gly Gly Arg Lys Gly Ala Lys Lys
250                 255                 260 gtg atg att gtc atc aca gat ggg gag tcc cac gac agc cca gac ctg      930
Val Met Ile Val Ile Thr Asp Gly Glu Ser His Asp Ser Pro Asp Leu
265                 270                 275                 280 gag aag gtg atc cag caa agc gaa aga gac aac gta aca aga tat gcg      978
Glu Lys Val Ile Gln Gln Ser Glu Arg Asp Asn Val Thr Arg Tyr Ala
                285                 290                 295 gtg gcc gtc ctg ggc tac tac aac cgc agg ggg atc aat cca gaa act     1026
Val Ala Val Leu Gly Tyr Tyr Asn Arg Arg Gly Ile Asn Pro Glu Thr
        300                 305                 310 ttt cta aat gaa atc aaa tac atc gcc agt gac cct gat gac aag cac     1074
Phe Leu Asn Glu Ile Lys Tyr Ile Ala Ser Asp Pro Asp Asp Lys His
    315                 320                 325 ttc ttc aat gtc act gat gag gct gcc ttg aag gac att gtc gat gcc     1122
Phe Phe Asn Val Thr Asp Glu Ala Ala Leu Lys Asp Ile Val Asp Ala
330                 335                 340 ctg ggg gac aga atc ttc agc ctg gaa ggc acc aac aag aac gag acc     1170
Leu Gly Asp Arg Ile Phe Ser Leu Glu Gly Thr Asn Lys Asn Glu Thr
345                 350                 355                 360 tcc ttt ggg ctg gag atg tca cag acg ggc ttt tcc tcg cac gtg gtg     1218
Ser Phe Gly Leu Glu Met Ser Gln Thr Gly Phe Ser Ser His Val Val
                365                 370                 375 gag gat ggg gtt ctg ctg gga gcc gtc ggt gcc tat gac tgg aat gga     1266
Glu Asp Gly Val Leu Leu Gly Ala Val Gly Ala Tyr Asp Trp Asn Gly
        380                 385                 390 gct gtg cta aag gag acg agt gcc ggg aag gtc att cct ctc cgc gag     1314
Ala Val Leu Lys Glu Thr Ser Ala Gly Lys Val Ile Pro Leu Arg Glu
    395                 400                 405 tcc tac ctg aaa gag ttc ccc gag gag ctc aag aac cat ggt gca tac     1362
Ser Tyr Leu Lys Glu Phe Pro Glu Glu Leu Lys Asn His Gly Ala Tyr
410                 415                 420 ctg ggg tac aca gtc aca tcg gtc gtg tcc tcc agg cag ggg cga gtg     1410
Leu Gly Tyr Thr Val Thr Ser Val Val Ser Ser Arg Gln Gly Arg Val
425                 430                 435                 440 tac gtg gcc gga gcc ccc cgg ttc aac cac acg ggc aag gtc atc ctg     1458
Tyr Val Ala Gly Ala Pro Arg Phe Asn His Thr Gly Lys Val Ile Leu
                445                 450                 455 ttc acc atg cac aac aac cgg agc ctc acc atc cac cag gct atg cgg     1506
Phe Thr Met His Asn Asn Arg Ser Leu Thr Ile His Gln Ala Met Arg
        460                 465                 470
```

```
                                              -continued
ggc cag cag ata ggc tct tac ttt ggg agt gaa atc acc tcg gtg gac     1554
Gly Gln Gln Ile Gly Ser Tyr Phe Gly Ser Glu Ile Thr Ser Val Asp
            475                 480                 485 atc gac ggc gac ggc gtg act gat gtc ctg ctg gtg ggc gca ccc atg     1602
Ile Asp Gly Asp Gly Val Thr Asp Val Leu Leu Val Gly Ala Pro Met
        490                 495                 500 tac ttc aac gag ggc cgt gag cga ggc aag gtg tac gtc tat gag ctg     1650
Tyr Phe Asn Glu Gly Arg Glu Arg Gly Lys Val Tyr Val Tyr Glu Leu
505                 510                 515                 520 aga cag aac cgg ttt gtt tat aac gga acg cta aag gat tca cac agt     1698
Arg Gln Asn Arg Phe Val Tyr Asn Gly Thr Leu Lys Asp Ser His Ser
                525                 530                 535 tac cag aat gcc cga ttt ggg tcc tcc att gcc tca gtt cga gac ctc     1746
Tyr Gln Asn Ala Arg Phe Gly Ser Ser Ile Ala Ser Val Arg Asp Leu
            540                 545                 550 aac cag gat tcc tac aat gac gtg gtg gtg gga gcc ccc ctg gag gac     1794
Asn Gln Asp Ser Tyr Asn Asp Val Val Val Gly Ala Pro Leu Glu Asp
        555                 560                 565 aac cac gca gga gcc atc tac atc ttc cac ggc ttc cga ggc agc atc     1842
Asn His Ala Gly Ala Ile Tyr Ile Phe His Gly Phe Arg Gly Ser Ile
570                 575                 580 ctg aag aca cct aag cag aga atc aca gcc tca gag ctg gct acc ggc     1890
Leu Lys Thr Pro Lys Gln Arg Ile Thr Ala Ser Glu Leu Ala Thr Gly
585                 590                 595                 600 ctc cag tat ttt ggc tgc agc atc cac ggg caa ttg gac ctc aat gag     1938
Leu Gln Tyr Phe Gly Cys Ser Ile His Gly Gln Leu Asp Leu Asn Glu
                605                 610                 615 gat ggg ctc atc gac ctg gca gtg gga gcc ctt ggc aac gct gtg att     1986
Asp Gly Leu Ile Asp Leu Ala Val Gly Ala Leu Gly Asn Ala Val Ile
            620                 625                 630 ctg tgg tcc cgc cca gtg gtt cag atc aat gcc agc ctc cac ttt gag     2034
Leu Trp Ser Arg Pro Val Val Gln Ile Asn Ala Ser Leu His Phe Glu
        635                 640                 645 cca tcc aag atc aac atc ttc cac aga gac tgc aag cgc agt ggc agg     2082
Pro Ser Lys Ile Asn Ile Phe His Arg Asp Cys Lys Arg Ser Gly Arg
650                 655                 660 gat gcc acc tgc ctg gcc gcc ttc ctc tgc ttc acg ccc atc ttc ctg     2130
Asp Ala Thr Cys Leu Ala Ala Phe Leu Cys Phe Thr Pro Ile Phe Leu
665                 670                 675                 680 gca ccc cat ttc caa aca aca act gtt ggc atc aga tac aac gcc acc     2178
Ala Pro His Phe Gln Thr Thr Thr Val Gly Ile Arg Tyr Asn Ala Thr
                685                 690                 695 atg gat gag agg cgg tat aca ccg agg gcc cac ctg gac gag ggc ggg     2226
Met Asp Glu Arg Arg Tyr Thr Pro Arg Ala His Leu Asp Glu Gly Gly
            700                 705                 710 gac cga ttc acc aac aga gcc gta ctg ctc tcc tcc ggc cag gag ctc     2274
Asp Arg Phe Thr Asn Arg Ala Val Leu Leu Ser Ser Gly Gln Glu Leu
        715                 720                 725 tgt gag cgg atc aac ttc cat gtc ctg gac act gct gac tac gtg aag     2322
Cys Glu Arg Ile Asn Phe His Val Leu Asp Thr Ala Asp Tyr Val Lys
730                 735                 740 cca gtg acc ttc tca gtc gag tat tcc ctg gag gac cct gac cat ggc     2370
Pro Val Thr Phe Ser Val Glu Tyr Ser Leu Glu Asp Pro Asp His Gly
745                 750                 755                 760 ccc atg ctg gac gac ggc tgg ccc acc act ctc aga gtc tcg gtg ccc     2418
Pro Met Leu Asp Asp Gly Trp Pro Thr Thr Leu Arg Val Ser Val Pro
                765                 770                 775 ttc tgg aac ggc tgc aat gag gat gag cac tgt gtc cct gac ctt gtg     2466
Phe Trp Asn Gly Cys Asn Glu Asp Glu His Cys Val Pro Asp Leu Val
            780                 785                 790
```

-continued

```
ttg gat gcc cgg agt gac ctg ccc acg gcc atg gag tac tgc cag agg         2514
Leu Asp Ala Arg Ser Asp Leu Pro Thr Ala Met Glu Tyr Cys Gln Arg
        795                 800                 805 gtg ctg agg aag cct gcg cag gac tgc tcc gca tac acg ctg tcc ttc         2562
Val Leu Arg Lys Pro Ala Gln Asp Cys Ser Ala Tyr Thr Leu Ser Phe
810                 815                 820 gac acc aca gtc ttc atc ata gag agc aca cgc cag cga gtg gcg gtg         2610
Asp Thr Thr Val Phe Ile Ile Glu Ser Thr Arg Gln Arg Val Ala Val
825                 830                 835                 840 gag gcc aca ctg gag aac agg ggc gag aac gcc tac agt acg gtc cta         2658
Glu Ala Thr Leu Glu Asn Arg Gly Glu Asn Ala Tyr Ser Thr Val Leu
                845                 850                 855 aat atc tcg cag tca gca aac ctg cag ttt gcc agc ttg atc cag aag         2706
Asn Ile Ser Gln Ser Ala Asn Leu Gln Phe Ala Ser Leu Ile Gln Lys
                860                 865                 870 gag gac tca gac ggt agc att gag tgt gtg aac gag gag agg agg ctc         2754
Glu Asp Ser Asp Gly Ser Ile Glu Cys Val Asn Glu Glu Arg Arg Leu
        875                 880                 885 cag aag caa gtc tgc aac gtc agc tat ccc ttc ttc cgg gcc aag gcc         2802
Gln Lys Gln Val Cys Asn Val Ser Tyr Pro Phe Phe Arg Ala Lys Ala
890                 895                 900 aag gtg gct ttc cgt ctt gat tcc gag ttc agc aaa tcc atc ttc cta         2850
Lys Val Ala Phe Arg Leu Asp Ser Glu Phe Ser Lys Ser Ile Phe Leu
905                 910                 915                 920 cac cac ctg gag atc gag ctc gct gca ggc agt gac agt aat gag cgg         2898
His His Leu Glu Ile Glu Leu Ala Ala Gly Ser Asp Ser Asn Glu Arg
                925                 930                 935 gac agc acc aag gaa gac aac gtg gcc ccc tta cgc ttc cac ctc aaa         2946
Asp Ser Thr Lys Glu Asp Asn Val Ala Pro Leu Arg Phe His Leu Lys
                940                 945                 950 tac gag gct gac gtc ctc ttc acc agg agc agc agc ctg agc cac tac         2994
Tyr Glu Ala Asp Val Leu Phe Thr Arg Ser Ser Ser Leu Ser His Tyr
        955                 960                 965 gag gtc aag ctc aac agc tcg ctg gag aga tac gat ggt atc ggg cct         3042
Glu Val Lys Leu Asn Ser Ser Leu Glu Arg Tyr Asp Gly Ile Gly Pro
970                 975                 980 ccc ttc agc tgc atc ttc agg atc cag aac ttg ggc ttg ttc ccc atc         3090
Pro Phe Ser Cys Ile Phe Arg Ile Gln Asn Leu Gly Leu Phe Pro Ile
985                 990                 995                 1000 cac ggg atg atg atg aag atc acc att ccc atc gcc acc agg agc ggc         3138
His Gly Met Met Met Lys Ile Thr Ile Pro Ile Ala Thr Arg Ser Gly
                1005                1010                1015 aac cgc cta ctg aag ctg agg gac ttc ctc acg gac gag gcg aac acg         3186
Asn Arg Leu Leu Lys Leu Arg Asp Phe Leu Thr Asp Glu Ala Asn Thr
                1020                1025                1030 tcc tgt aac atc tgg ggc aat agc act gag tac cgg ccc acc cca gtg         3234
Ser Cys Asn Ile Trp Gly Asn Ser Thr Glu Tyr Arg Pro Thr Pro Val
        1035                1040                1045 gag gaa gac ttg cgt cgt gct cca cag ctg aat cac agc aac tct gat         3282
Glu Glu Asp Leu Arg Arg Ala Pro Gln Leu Asn His Ser Asn Ser Asp
1050                1055                1060 gtc gtc tcc atc aac tgc aat ata cgg ctg gtc ccc aac cag gaa atc         3330
Val Val Ser Ile Asn Cys Asn Ile Arg Leu Val Pro Asn Gln Glu Ile
1065                1070                1075                1080 aat ttc cat cta ctg ggg aac ctg tgg ttg agg tcc cta aaa gca ctc         3378
Asn Phe His Leu Leu Gly Asn Leu Trp Leu Arg Ser Leu Lys Ala Leu
                1085                1090                1095 aag tac aaa tcc atg aaa atc atg gtc aac gca gcc ttg cag agg cag         3426
Lys Tyr Lys Ser Met Lys Ile Met Val Asn Ala Ala Leu Gln Arg Gln
        1100                1105                1110
```

-continued

```
ttc cac agc ccc ttc atc ttc cgt gag gag gat ccc agc cgc cag atc    3474
Phe His Ser Pro Phe Ile Phe Arg Glu Glu Asp Pro Ser Arg Gln Ile
    1115                1120                1125 gag ttt gag atc tcc aag caa gag gac tgg cag gtc ccc atc tgg atc    3522
Glu Phe Glu Ile Ser Lys Gln Glu Asp Trp Gln Val Pro Ile Trp Ile
1130                1135                1140 att gta ggc agc acc ctg ggg ggc ctc cta ctg ctg gcc ctg ctg gtc    3570
Ile Val Gly Ser Thr Leu Gly Gly Leu Leu Leu Leu Ala Leu Leu Val
1145                1150                1155                1160 ctg gca ctg cgg aag ctc ggc ttc ttt aga agt gcc agg cgc agg agg    3618
Leu Ala Leu Arg Lys Leu Gly Phe Phe Arg Ser Ala Arg Arg Arg Arg
                1165                1170                1175 gag cct ggt ctg gac ccc acc ccc aaa gtg ctg gag tgaggctcca         3664
Glu Pro Gly Leu Asp Pro Thr Pro Lys Val Leu Glu
            1180                1185 gaggagactt tgagttgatg ggggccagga caccagtcca ggtagtgttg agacccaggc   3724
ctgtggcccc accagctggg agcggagagg aagccagctg gctttgcact tgacctcatc   3784
tcccgagcaa tggcgcctgc tccctccaga atggaactca agctggtttt aagtggaact   3844
gcctactggg agactgggac acctttacac agacccctag ggatttaaag ggacaccccct  3904
acacacaccc aggcccacgc caaggcctcc ctcaggctct gtggagggca tttgctgccc   3964
cagctactaa ggtgctagg                                                3983
```

<210> SEQ ID NO 2
<211> LENGTH: 1188
<212> TYPE: PRT
<213> ORGANISM: human

<400> SEQUENCE: 2

```
Met Asp Leu Pro Arg Gly Leu Val Val Ala Trp Ala Leu Ser Leu Trp
1               5                   10                  15

Pro Gly Phe Thr Asp Thr Phe Asn Met Asp Thr Arg Lys Pro Arg Val
            20                  25                  30

Ile Pro Gly Ser Arg Thr Ala Phe Phe Gly Tyr Thr Val Gln Gln His
        35                  40                  45

Asp Ile Ser Gly Asn Lys Trp Leu Val Val Gly Ala Pro Leu Glu Thr
    50                  55                  60

Asn Gly Tyr Gln Lys Thr Gly Asp Val Tyr Lys Cys Pro Val Ile His
65                  70                  75                  80

Gly Asn Cys Thr Lys Leu Asn Leu Gly Arg Val Thr Leu Ser Asn Val
                85                  90                  95

Ser Glu Arg Lys Asp Asn Met Arg Leu Gly Leu Ser Leu Ala Thr Asn
            100                 105                 110

Pro Lys Asp Asn Ser Phe Leu Ala Cys Ser Pro Leu Trp Ser His Glu
        115                 120                 125

Cys Gly Ser Ser Tyr Tyr Thr Thr Gly Met Cys Ser Arg Val Asn Ser
    130                 135                 140

Asn Phe Arg Phe Ser Lys Thr Val Ala Pro Ala Leu Gln Arg Cys Gln
145                 150                 155                 160

Thr Tyr Met Asp Ile Val Ile Val Leu Asp Gly Ser Asn Ser Ile Tyr
                165                 170                 175

Pro Trp Val Glu Val Gln His Phe Leu Ile Asn Ile Leu Lys Lys Phe
            180                 185                 190

Tyr Ile Gly Pro Gly Gln Ile Gln Val Gly Val Val Gln Tyr Gly Glu
        195                 200                 205
```

```
Asp Val Val His Glu Phe His Leu Asn Asp Tyr Arg Ser Val Lys Asp
    210                 215                 220

Val Val Glu Ala Ala Ser His Ile Glu Gln Arg Gly Gly Thr Glu Thr
225                 230                 235                 240

Arg Thr Ala Phe Gly Ile Glu Phe Ala Arg Ser Glu Ala Phe Gln Lys
                245                 250                 255

Gly Gly Arg Lys Gly Ala Lys Lys Val Met Ile Val Ile Thr Asp Gly
            260                 265                 270

Glu Ser His Asp Ser Pro Asp Leu Glu Lys Val Ile Gln Gln Ser Glu
        275                 280                 285

Arg Asp Asn Val Thr Arg Tyr Ala Val Ala Val Leu Gly Tyr Tyr Asn
    290                 295                 300

Arg Arg Gly Ile Asn Pro Glu Thr Phe Leu Asn Glu Ile Lys Tyr Ile
305                 310                 315                 320

Ala Ser Asp Pro Asp Asp Lys His Phe Phe Asn Val Thr Asp Glu Ala
                325                 330                 335

Ala Leu Lys Asp Ile Val Asp Ala Leu Gly Asp Arg Ile Phe Ser Leu
            340                 345                 350

Glu Gly Thr Asn Lys Asn Glu Thr Ser Phe Gly Leu Glu Met Ser Gln
        355                 360                 365

Thr Gly Phe Ser Ser His Val Val Glu Asp Gly Val Leu Leu Gly Ala
    370                 375                 380

Val Gly Ala Tyr Asp Trp Asn Gly Ala Val Leu Lys Glu Thr Ser Ala
385                 390                 395                 400

Gly Lys Val Ile Pro Leu Arg Glu Ser Tyr Leu Lys Glu Phe Pro Glu
                405                 410                 415

Glu Leu Lys Asn His Gly Ala Tyr Leu Gly Tyr Thr Val Thr Ser Val
            420                 425                 430

Val Ser Ser Arg Gln Gly Arg Val Tyr Val Ala Gly Ala Pro Arg Phe
        435                 440                 445

Asn His Thr Gly Lys Val Ile Leu Phe Thr Met His Asn Asn Arg Ser
    450                 455                 460

Leu Thr Ile His Gln Ala Met Arg Gly Gln Gln Ile Gly Ser Tyr Phe
465                 470                 475                 480

Gly Ser Glu Ile Thr Ser Val Asp Ile Asp Gly Asp Gly Val Thr Asp
                485                 490                 495

Val Leu Leu Val Gly Ala Pro Met Tyr Phe Asn Glu Gly Arg Glu Arg
            500                 505                 510

Gly Lys Val Tyr Val Tyr Glu Leu Arg Gln Asn Arg Phe Val Tyr Asn
        515                 520                 525

Gly Thr Leu Lys Asp Ser His Ser Tyr Gln Asn Ala Arg Phe Gly Ser
    530                 535                 540

Ser Ile Ala Ser Val Arg Asp Leu Asn Gln Asp Ser Tyr Asn Asp Val
545                 550                 555                 560

Val Val Gly Ala Pro Leu Glu Asp Asn His Ala Gly Ala Ile Tyr Ile
                565                 570                 575

Phe His Gly Phe Arg Gly Ser Ile Leu Lys Thr Pro Lys Gln Arg Ile
            580                 585                 590

Thr Ala Ser Glu Leu Ala Thr Gly Leu Gln Tyr Phe Gly Cys Ser Ile
        595                 600                 605

His Gly Gln Leu Asp Leu Asn Glu Asp Gly Leu Ile Asp Leu Ala Val
    610                 615                 620
```

-continued

```
Gly Ala Leu Gly Asn Ala Val Ile Leu Trp Ser Arg Pro Val Val Gln
625                 630                 635                 640

Ile Asn Ala Ser Leu His Phe Glu Pro Ser Lys Ile Asn Ile Phe His
            645                 650                 655

Arg Asp Cys Lys Arg Ser Gly Arg Asp Ala Thr Cys Leu Ala Ala Phe
                660                 665                 670

Leu Cys Phe Thr Pro Ile Phe Leu Ala Pro His Phe Gln Thr Thr Thr
            675                 680                 685

Val Gly Ile Arg Tyr Asn Ala Thr Met Asp Glu Arg Tyr Thr Pro
        690                 695                 700

Arg Ala His Leu Asp Glu Gly Gly Asp Arg Phe Thr Asn Arg Ala Val
705                 710                 715                 720

Leu Leu Ser Ser Gly Gln Glu Leu Cys Glu Arg Ile Asn Phe His Val
                725                 730                 735

Leu Asp Thr Ala Asp Tyr Val Lys Pro Val Thr Phe Ser Val Glu Tyr
            740                 745                 750

Ser Leu Glu Asp Pro Asp His Gly Pro Met Leu Asp Asp Gly Trp Pro
        755                 760                 765

Thr Thr Leu Arg Val Ser Val Pro Phe Trp Asn Gly Cys Asn Glu Asp
770                 775                 780

Glu His Cys Val Pro Asp Leu Val Leu Asp Ala Arg Ser Asp Leu Pro
785                 790                 795                 800

Thr Ala Met Glu Tyr Cys Gln Arg Val Leu Arg Lys Pro Ala Gln Asp
                805                 810                 815

Cys Ser Ala Tyr Thr Leu Ser Phe Asp Thr Thr Val Phe Ile Ile Glu
            820                 825                 830

Ser Thr Arg Gln Arg Val Ala Val Glu Ala Thr Leu Glu Asn Arg Gly
        835                 840                 845

Glu Asn Ala Tyr Ser Thr Val Leu Asn Ile Ser Gln Ser Ala Asn Leu
        850                 855                 860

Gln Phe Ala Ser Leu Ile Gln Lys Glu Asp Ser Asp Gly Ser Ile Glu
865                 870                 875                 880

Cys Val Asn Glu Glu Arg Arg Leu Gln Lys Gln Val Cys Asn Val Ser
                885                 890                 895

Tyr Pro Phe Phe Arg Ala Lys Ala Lys Val Ala Phe Arg Leu Asp Ser
            900                 905                 910

Glu Phe Ser Lys Ser Ile Phe Leu His His Leu Glu Ile Glu Leu Ala
        915                 920                 925

Ala Gly Ser Asp Ser Asn Glu Arg Asp Ser Thr Lys Glu Asp Asn Val
930                 935                 940

Ala Pro Leu Arg Phe His Leu Lys Tyr Glu Ala Asp Val Leu Phe Thr
945                 950                 955                 960

Arg Ser Ser Ser Leu Ser His Tyr Glu Val Lys Leu Asn Ser Ser Leu
                965                 970                 975

Glu Arg Tyr Asp Gly Ile Gly Pro Pro Phe Ser Cys Ile Phe Arg Ile
            980                 985                 990

Gln Asn Leu Gly Leu Phe Pro Ile His Gly Met Met Met Lys Ile Thr
        995                 1000                1005

Ile Pro Ile Ala Thr Arg Ser Gly Asn Arg Leu Leu Lys Leu Arg Asp
    1010                1015                1020

Phe Leu Thr Asp Glu Ala Asn Thr Ser Cys Asn Ile Trp Gly Asn Ser
1025                1030                1035                1040
```

```
Thr Glu Tyr Arg Pro Thr Pro Val Glu Glu Asp Leu Arg Arg Ala Pro
                1045            1050                1055

Gln Leu Asn His Ser Asn Ser Asp Val Val Ser Ile Asn Cys Asn Ile
        1060            1065                1070

Arg Leu Val Pro Asn Gln Glu Ile Asn Phe His Leu Leu Gly Asn Leu
    1075            1080                1085

Trp Leu Arg Ser Leu Lys Ala Leu Lys Tyr Lys Ser Met Lys Ile Met
  1090            1095                1100

Val Asn Ala Ala Leu Gln Arg Gln Phe His Ser Pro Phe Ile Phe Arg
1105            1110                1115                1120

Glu Glu Asp Pro Ser Arg Gln Ile Glu Phe Glu Ile Ser Lys Gln Glu
                1125            1130                1135

Asp Trp Gln Val Pro Ile Trp Ile Ile Val Gly Ser Thr Leu Gly Gly
            1140            1145                1150

Leu Leu Leu Leu Ala Leu Leu Val Leu Ala Leu Arg Lys Leu Gly Phe
        1155            1160                1165

Phe Arg Ser Ala Arg Arg Arg Glu Pro Gly Leu Asp Pro Thr Pro
    1170            1175                1180

Lys Val Leu Glu
1185

<210> SEQ ID NO 3
<211> LENGTH: 24
<212> TYPE: PRT
<213> ORGANISM: Human

<400> SEQUENCE: 3

Lys Leu Gly Phe Phe Arg Ser Ala Arg Arg Arg Glu Pro Gly Leu
1               5                   10                  15

Asp Pro Thr Pro Lys Val Leu Glu
            20

<210> SEQ ID NO 4
<211> LENGTH: 5
<212> TYPE: PRT
<213> ORGANISM: Human

<400> SEQUENCE: 4

Gly Phe Phe Arg Ser
1               5

<210> SEQ ID NO 5
<211> LENGTH: 5
<212> TYPE: PRT
<213> ORGANISM: Human

<400> SEQUENCE: 5

Gly Phe Phe Lys Arg
1               5
```